United States Patent
Shimizu

(10) Patent No.: US 10,550,058 B2
(45) Date of Patent: *Feb. 4, 2020

(54) METHOD FOR PRODUCING ACETIC ACID

(71) Applicant: DAICEL CORPORATION, Osaka-shi, Osaka (JP)

(72) Inventor: Masahiko Shimizu, Himeji (JP)

(73) Assignee: DAICEL CORPORATION, Osaka-Shi (JP)

(*) Notice: Subject to any disclaimer, the term of this patent is extended or adjusted under 35 U.S.C. 154(b) by 0 days.

This patent is subject to a terminal disclaimer.

(21) Appl. No.: 15/542,610

(22) PCT Filed: May 25, 2017

(86) PCT No.: PCT/JP2017/019577
§ 371 (c)(1),
(2) Date: Jul. 10, 2017

(87) PCT Pub. No.: WO2018/163449
PCT Pub. Date: Sep. 13, 2018

(65) Prior Publication Data
US 2018/0258021 A1    Sep. 13, 2018

(30) Foreign Application Priority Data
Mar. 8, 2017   (JP) ................ 2017-044342

(51) Int. Cl.
C07C 51/12    (2006.01)
C07C 51/44    (2006.01)

(52) U.S. Cl.
CPC .............. *C07C 51/12* (2013.01); *C07C 51/44* (2013.01)

(58) Field of Classification Search
None
See application file for complete search history.

(56) References Cited

U.S. PATENT DOCUMENTS

| | | | |
|---|---|---|---|
| 5,625,095 A | 4/1997 | Miura et al. |
| 5,723,660 A | 3/1998 | Morimoto et al. |
| 5,756,836 A | 5/1998 | Shimizu et al. |
| 5,916,422 A | 6/1999 | Kimura et al. |
| 6,143,930 A | 11/2000 | Singh et al. |
| 6,303,813 B1 | 10/2001 | Scates et al. |
| 6,458,996 B1 | 10/2002 | Muskett |
| 7,683,212 B2 | 3/2010 | Kojima et al. |
| 9,006,483 B2 | 4/2015 | Shimizu et al. |
| 9,073,843 B2 | 7/2015 | Shimizu et al. |
| 2007/0093676 A1 | 4/2007 | Kojima et al. |
| 2013/0261334 A1 | 10/2013 | Shimizu et al. |
| 2015/0025270 A1 | 1/2015 | Shimizu et al. |
| 2015/0299084 A1 | 10/2015 | Shimizu et al. |
| 2016/0102036 A1 | 4/2016 | Shaver |
| 2016/0221909 A1 | 8/2016 | Shaver et al. |

FOREIGN PATENT DOCUMENTS

| | | |
|---|---|---|
| EP | 0645362 A1 | 3/1995 |
| EP | 0687662 A2 | 12/1995 |
| EP | 0768295 A1 | 4/1997 |
| EP | 0 976 711 A1 | 2/2000 |
| EP | 2937329 A1 | 10/2015 |
| JP | 7-25813 A | 1/1995 |
| JP | 7-133249 A | 5/1995 |
| JP | 8-20555 A | 1/1996 |
| JP | H08-059542 A | 3/1996 |
| JP | 2001-508405 A | 6/2001 |
| JP | 2003-508363 A | 3/2003 |
| JP | 2006-182691 A | 7/2006 |
| JP | 2016-164137 A | 9/2016 |
| JP | 2016-539078 A | 12/2016 |
| WO | WO 96/33965 A1 | 10/1996 |
| WO | WO 98/17619 A2 | 4/1998 |
| WO | WO 2012/081417 A1 | 6/2012 |

(Continued)

OTHER PUBLICATIONS

Machine translation JP2003-508363.*
Machine translation WO 2013/137236.*
English tranlsation of the Written Opinion dated Oct. 6, 2017, in PCT International Application No. PCT/JP2017/019577.
Japanese Notification of Reasons for Rejection for Application No. 2017-536033, dated Jul. 10, 2018, with English language translation.
Japanese Notification of Reasons for Refusal for counterpart Application No. 2017-536033, dated Feb. 12, 2019, with an English language translation.

(Continued)

*Primary Examiner* — Ana Z Muresan
(74) *Attorney, Agent, or Firm* — Birch, Stewart, Kolasch & Birch, LLP

(57) ABSTRACT

It is intended to provide a method capable of industrially and efficiently producing acetic acid having a good potassium permanganate test value without a large cost.

A method for producing acetic acid according to the present invention is a method for producing acetic acid comprising: a carbonylation reaction step; an evaporation step; a lower boiling point component removal step; and a first overhead stream recycle step of recycling at least a portion of an aqueous phase and/or an organic phase obtained by condensing a first overhead stream obtained in the lower boiling point component removal step to a reaction vessel, wherein a crotonaldehyde concentration in a first acetic acid stream obtained in the lower boiling point component removal step is controlled to not more than 2.2 ppm by mass. The catalyst system may further contain an ionic iodide. The method for producing acetic acid may further comprise an acetaldehyde separation and removal step of distilling at least a portion of the aqueous phase and/or the organic phase obtained by condensing the first overhead stream to separate and remove acetaldehyde.

21 Claims, 5 Drawing Sheets

(56) References Cited

FOREIGN PATENT DOCUMENTS

| WO | WO 2013/137236 A1 | 9/2013 |
| WO | WO 2014/097867 A1 | 6/2014 |
| WO | WO 2016/054608 A1 | 4/2016 |
| WO | WO 2016/122728 A1 | 8/2016 |

OTHER PUBLICATIONS

Extended European Search Report, dated Mar. 1. 2019, for European Application No. 17739174.5.
International Search Report, issued in PCT/JP2017/019577, dated Jun. 27, 2017.

\* cited by examiner

[Figure 1]
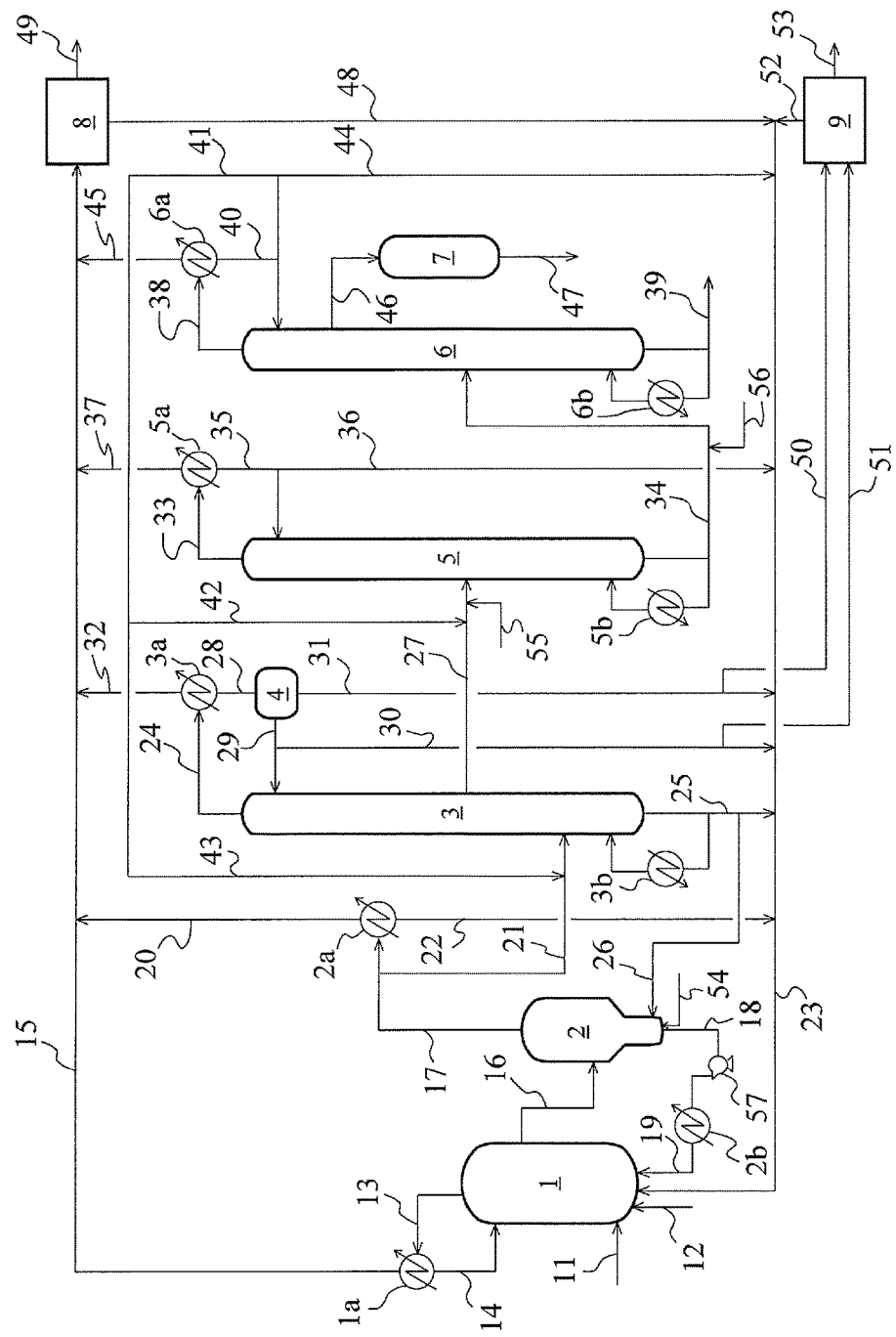

[Figure 2]
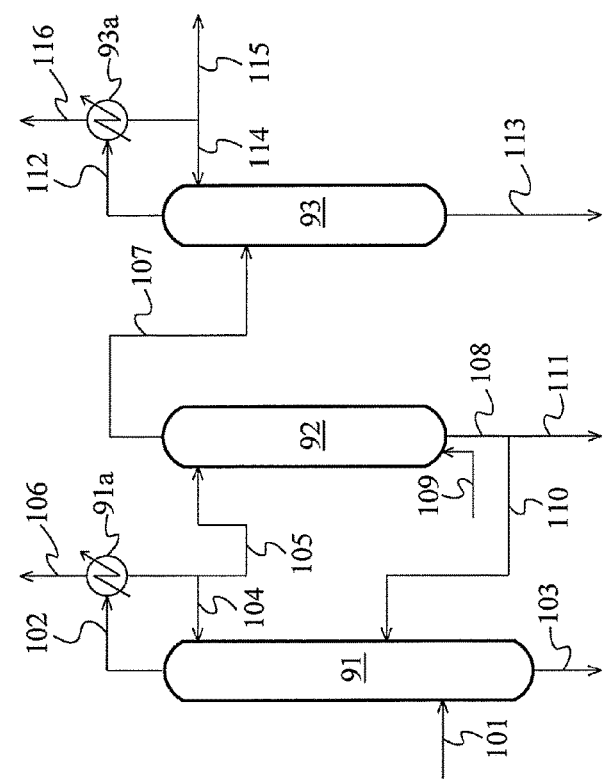

[Figure 3]
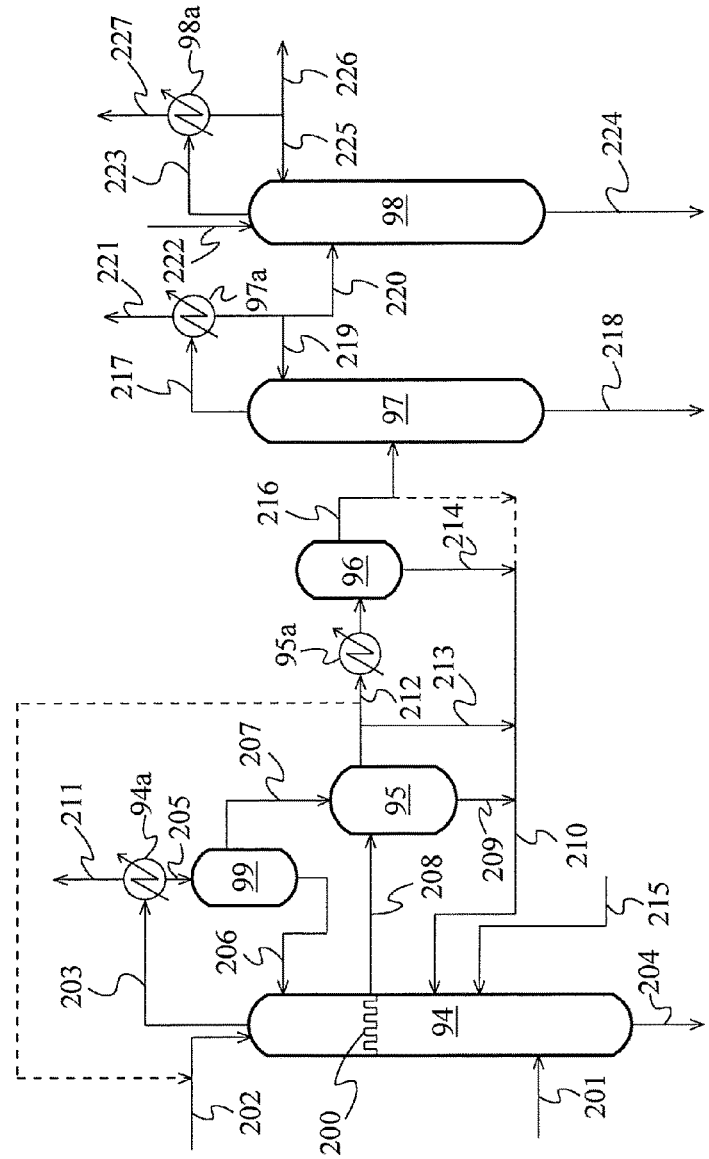

[Figure 4]
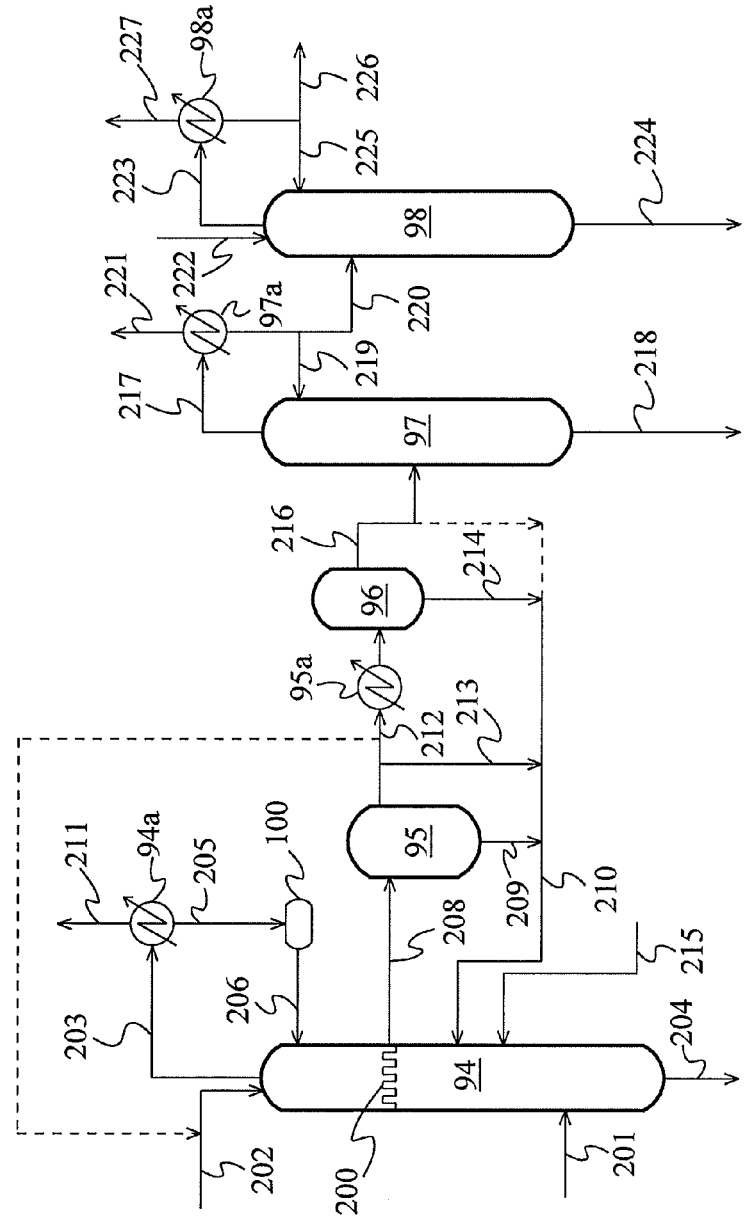

[Figure 5]
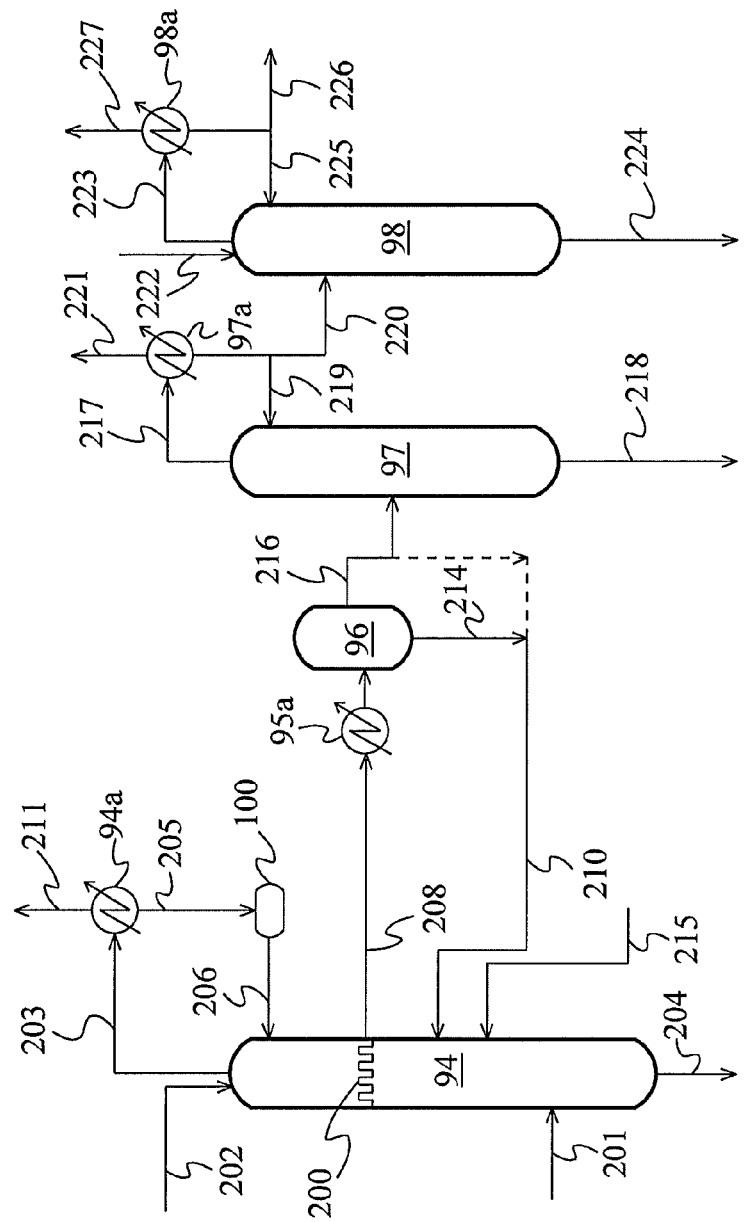

METHOD FOR PRODUCING ACETIC ACID

TECHNICAL FIELD

The present invention relates to a method for producing acetic acid. The present application claims the priority of Japanese Patent Application No. 2017-044342 filed in Japan on Mar. 8, 2017, the contents of which are incorporated herein by reference in their entirety.

BACKGROUND ART

A carbonylation process of a methanol method (an acetic acid process of a methanol method) is known as an industrial method for producing acetic acid. In this process, for example, methanol and carbon monoxide are reacted in the presence of a catalyst in a reaction vessel to produce acetic acid. The reaction mixture is evaporated in an evaporator, and the vapor phase is purified in a lower boiling point component removal column and subsequently in a dehydration column so that product acetic acid is prepared. Alternatively, product acetic acid is prepared via a higher boiling point component removal column subsequent to the dehydration column, and further, a product column.

In such an acetic acid production process, acetaldehyde is produced as a by-product in a reaction system, and the aldol condensation of acetaldehyde produces crotonaldehyde. Crotonaldehyde causes deterioration in a potassium permanganate test value (permanganate time) of product acetic acid. Furthermore, crotonaldehyde reacts with acetaldehyde to produce 2-ethyl crotonaldehyde. Although 2-ethyl crotonaldehyde also causes deterioration in the potassium permanganate test value of product acetic acid, the degree of potassium permanganate test deterioration per mass of 2-ethyl crotonaldehyde is much smaller than that of crotonaldehyde. Conventionally, the following two general methods have been industrially adopted in order to decrease crotonaldehyde or 2-ethyl crotonaldehyde: (i) a method for separating and removing acetaldehyde produced as a by-product in a reaction system from methyl iodide in a purification step, and decreasing acetaldehyde in methyl iodide to be recycled to the reaction system to suppress the production of crotonaldehyde in the reaction system; and (ii) a method for directly subjecting crotonaldehyde contained in crude acetic acid obtained during a purification step to oxidative decomposition using ozone (Patent Literatures 1 and 2). However, both separation and removal equipment of acetaldehyde and ozonation equipment are expensive. Conventionally, an increase in the potassium permanganate test value of product acetic acid has thoroughly depended on these methods, which has led to an increase in the equipment cost.

CITATION LIST

Patent Literature

Patent Literature 1: Japanese Patent Laid-Open No. 07-25813
Patent Literature 2: National Publication of International Patent Application No. 2001-508405

SUMMARY OF INVENTION

Technical Problem

Therefore, an object of the present invention is to provide a method capable of industrially and efficiently producing acetic acid having a good potassium permanganate test value without a large cost.

Solution to Problem

In order to attain the object, the present inventors conducted diligent studies to find that high-quality acetic acid having a good potassium permanganate test value can be industrially and efficiently produced without providing large-scale disposal equipment by controlling a crotonaldehyde concentration in an acetic acid stream (first acetic acid stream) obtained by lower boiling point component removal in a lower boiling point component removal column to not more than a specific value, or by setting the reflux ratio of a dehydration column to not less than a specific value, in a carbonylation process of a methanol method. The present invention was accomplished based on the above findings.

Specifically, the present invention provides a method for producing acetic acid comprising:

a carbonylation reaction step of reacting methanol with carbon monoxide in the presence of a catalyst system containing a metal catalyst and methyl iodide, as well as acetic acid, methyl acetate, and water in a reaction vessel to produce acetic acid;

an evaporation step of separating a reaction mixture obtained in the carbonylation reaction step into a vapor stream and a residual liquid stream in an evaporator;

a lower boiling point component removal step of separating the vapor stream by a first distillation column into a first overhead stream rich in at least one lower boiling point component selected from methyl iodide and acetaldehyde, and a first acetic acid stream rich in acetic acid, and condensing and separating the first overhead stream to obtain an aqueous phase and an organic phase; and a first overhead stream recycle step of recycling at least a portion of the aqueous phase and/or the organic phase obtained by condensing the first overhead stream to the reaction vessel, wherein a crotonaldehyde concentration in the first acetic acid stream is controlled to not more than 2.2 ppm by mass (hereinafter, may also be referred to as a "first method for producing acetic acid").

The present invention provides a method for producing acetic acid comprising:

a carbonylation reaction step of reacting methanol with carbon monoxide in the presence of a catalyst system containing a metal catalyst and methyl iodide, as well as acetic acid, methyl acetate, and water in a reaction vessel to produce acetic acid;

an evaporation step of separating a reaction mixture obtained in the carbonylation reaction step into a vapor stream and a residual liquid stream in an evaporator;

a lower boiling point component removal step of separating the vapor stream by a first distillation column into a first overhead stream rich in at least one lower boiling point component selected from methyl iodide and acetaldehyde, and a first acetic acid stream rich in acetic acid, and condensing and separating the first overhead stream to obtain an aqueous phase and an organic phase;

a dehydration step of separating the first acetic acid stream by a second distillation column into a second overhead stream rich in water and a second acetic acid stream more enriched with acetic acid than the first acetic acid stream; and an overhead stream recycle step of recycling at least a portion of the aqueous phase and/or the organic phase obtained by condensing the first overhead stream, and/or a portion of the second overhead stream to the reaction vessel, wherein a crotonaldehyde concentration in the first acetic acid stream is controlled to not more than 2.2 ppm by mass, and/or a reflux ratio of the second distillation column is controlled to not less than 0.32 (hereinafter, may also be referred to as "second method for producing acetic acid").

A crotonaldehyde concentration in the second acetic acid stream is, for example, not more than 2.0 ppm by mass.

A 2-ethyl crotonaldehyde concentration in the second acetic acid stream is, for example, not more than 3.0 ppm by mass.

A ratio ($C_{CR}/C_{ECR}$) of the crotonaldehyde concentration $C_{CR}$ (ppm by mass) to the 2-ethyl crotonaldehyde concentration $C_{ECR}$ (ppm by mass) in the second acetic acid stream is, for example, not more than 35.

A butyl acetate concentration in the second acetic acid stream is, for example, not more than 15 ppm by mass.

A ratio ($C_{CR}/C_{BA}$) of the crotonaldehyde concentration $C_{CR}$ (ppm by mass) to the butyl acetate concentration $C_{BA}$ (ppm by mass) in the second acetic acid stream is, for example, not more than 2.0.

In the first and second methods for producing acetic acid, the catalyst system may further contain an ionic iodide.

The first and second methods for producing acetic acid may further comprise an acetaldehyde separation and removal step of distilling at least a portion of the aqueous phase and/or the organic phase obtained by condensing the first overhead stream, to separate and remove acetaldehyde. In this case, at least a portion of a residual liquid after separating and removing the acetaldehyde from at least a portion of the aqueous phase and/or the organic phase may be recycled to the reaction vessel.

For an operating condition of the first distillation column, when only the aqueous phase is refluxed to the first distillation column, the reflux ratio of the aqueous phase may be not less than 2; when only the organic phase is refluxed, the reflux ratio of the organic phase may be not less than 1; and when both the aqueous phase and the organic phase are refluxed, the total reflux ratio of the aqueous phase and the organic phase may be not less than 1.5.

A hydrogen partial pressure of the reaction vessel is, for example, not less than 0.01 MPa (absolute pressure).

An acetaldehyde concentration in a reaction mixture liquid of the reaction vessel is, for example, not more than 500 ppm by mass.

A 2-ethyl crotonaldehyde concentration in the first acetic acid stream is, for example, not more than 3.0 ppm by mass.

A ratio ($C_{CR}/C_{ECR}$) of the crotonaldehyde concentration $C_{CR}$ (ppm by mass) to the 2-ethyl crotonaldehyde concentration $C_{ECR}$ (ppm by mass) in the first acetic acid stream is, for example, not more than 35.

A butyl acetate concentration in the first acetic acid stream is, for example, not more than 15 ppm by mass.

A ratio ($C_{CR}/C_{BA}$) of the crotonaldehyde concentration $C_{CR}$ (ppm by mass) to the butyl acetate concentration $C_{BA}$ (ppm by mass) in the first acetic acid stream is, for example, not more than 2.0.

Advantageous Effects of Invention

According to the present invention, a crotonaldehyde concentration in an acetic acid stream (first acetic acid stream) obtained in a lower boiling point component removal column is controlled to not more than a specific value, or the reflux ratio of a dehydration column is controlled to not less than a specific value, which can industrially and efficiently produce high-quality acetic acid having a good potassium permanganate test value (also referred to as a "permanganate time" or a "chameleon time") without providing large-scale acetaldehyde removal equipment and ozonation equipment.

BRIEF DESCRIPTION OF DRAWINGS

FIG. 1 is an acetic acid production flow diagram showing one embodiment of the present invention.

FIG. 2 is a schematic flow diagram showing one example of an acetaldehyde separation and removal system.

FIG. 3 is a schematic flow diagram showing another example of the acetaldehyde separation and removal system.

FIG. 4 is a schematic flow diagram showing a further alternative example of the acetaldehyde separation and removal system.

FIG. 5 is a schematic flow diagram showing a further alternative example of the acetaldehyde separation and removal system.

DESCRIPTION OF EMBODIMENTS

A first method for producing acetic acid according to the present invention comprises: a carbonylation reaction step of reacting methanol with carbon monoxide in the presence of a catalyst system containing a metal catalyst and methyl iodide, as well as acetic acid, methyl acetate, and water in a reaction vessel to produce acetic acid; an evaporation step of separating a reaction mixture obtained in the carbonylation reaction step into a vapor stream and a residual liquid stream in an evaporator; a lower boiling point component removal step of separating the vapor stream by a first distillation column into a first overhead stream rich in at least one lower boiling point component selected from methyl iodide and acetaldehyde, and a first acetic acid stream rich in acetic acid, and condensing and separating the first overhead stream to obtain an aqueous phase and an organic phase; and a first overhead stream recycle step of recycling at least a portion of the aqueous phase and/or the organic phase obtained by condensing the first overhead stream to the reaction vessel, wherein a crotonaldehyde concentration in the first acetic acid stream is controlled to not more than 2.2 ppm by mass.

A second method for producing acetic acid according to the present invention comprises: a carbonylation reaction step of reacting methanol with carbon monoxide in the presence of a catalyst system containing a metal catalyst and methyl iodide, as well as acetic acid, methyl acetate, and water in a reaction vessel to produce acetic acid; an evaporation step of separating a reaction mixture obtained in the carbonylation reaction step into a vapor stream and a residual liquid stream in an evaporator; a lower boiling point component removal step of separating the vapor stream by a first distillation column (lower boiling point component removal column) into a first overhead stream rich in at least one lower boiling point component selected from methyl iodide and acetaldehyde, and a first acetic acid stream rich in acetic acid, and condensing and separating the first overhead stream to obtain an aqueous phase and an organic phase; a dehydration step of separating the first acetic acid stream by a second distillation column (dehydration column) into a second overhead stream rich in water and a second acetic acid stream more enriched with acetic acid than the first acetic acid stream; and an overhead stream recycle step of recycling at least a portion of the aqueous phase and/or the organic phase obtained by condensing the first overhead stream, and/or a portion of the second overhead stream to the reaction vessel, wherein (1) a crotonaldehyde concentration in the first acetic acid stream is controlled to not more than 2.2 ppm by mass, and/or (2) a reflux ratio of the second distillation column (dehydration column) is controlled to not less than 0.32. In the first and second methods for producing acetic acid according to the present invention (hereinafter, these may be collectively referred to as a "method for producing acetic acid according to the present invention"), the catalyst system may further contain an ionic iodide.

The method for producing acetic acid according to the present invention may further comprise an acetaldehyde separation and removal step of distilling at least a portion of the aqueous phase and/or the organic phase to separate and remove acetaldehyde. In this case, at least a portion of a residual liquid after separating and removing the acetaldehyde from at least a portion of the aqueous phase and/or the organic phase may be recycled to the reaction vessel.

By controlling the crotonaldehyde concentration in the first acetic acid stream obtained in the lower boiling point component removal step to a low concentration of not more than 2.2 ppm by mass, a crotonaldehyde concentration in the second acetic acid stream obtained by separating and removing water in the dehydration step can be decreased to, for example, not more than 2.0 ppm by mass, and a potassium permanganate test value of the second acetic acid stream can be increased. Therefore, acetaldehyde removal equipment and ozonation equipment which have been conventionally used for an improvement in the potassium permanganate test value can be made small-scale, or omitted. Since acetic acid having a high potassium permanganate test value can be obtained through only the lower boiling point component removal column and the dehydration column, a subsequent higher boiling point component removal column and a product column (finishing column) can be made small-scale, or omitted. The crotonaldehyde concentration in the first acetic acid stream is preferably not more than 2.0 ppm by mass, more preferably not more than 1.8 ppm by mass, further preferably not more than 1.5 ppm by mass, particularly preferably not more than 1.2 ppm by mass (for example, not more than 1.0 ppm by mass, or not more than 0.8 ppm by mass, among others, not more than 0.5 ppm by mass). When the reflux ratio of the second distillation column (dehydration column) is controlled to not less than 0.32, the crotonaldehyde concentration in the first acetic acid stream may be, for example, not more than 5 ppm by mass (particularly, not more than 2.5 ppm by mass), and is preferably within the ranges described above.

Examples of a method for decreasing the crotonaldehyde concentration in the first acetic acid stream include increasing the hydrogen partial pressure of the reaction vessel. Since crotonaldehyde is hydrogenated by increasing the hydrogen partial pressure of the reaction vessel, and a crotonaldehyde concentration in a reaction mixture liquid (liquid phase of reaction mixture; reaction medium) is decreased, a crotonaldehyde concentration in a charging mixture of the first distillation column is also decreased. Therefore, the crotonaldehyde concentration in the first acetic acid stream obtained by lower boiling point component removal in the first distillation column is also decreased. The hydrogen partial pressure of the reaction vessel is, for example, not less than 0.01 MPa (absolute pressure), preferably not less than 0.015 MPa (absolute pressure), more preferably not less than 0.02 MPa (absolute pressure), further preferably not less than 0.04 MPa (absolute pressure), particularly preferably not less than 0.06 MPa (absolute pressure) [for example, not less than 0.07 MPa (absolute pressure)]. The upper limit of the hydrogen partial pressure of the reaction vessel is, for example, 0.5 MPa (absolute pressure) [particularly, 0.2 MPa (absolute pressure)].

Another examples of the method for decreasing the crotonaldehyde concentration in the first acetic acid stream include increasing the reflux ratio in the lower boiling point component removal column. Since crotonaldehyde (boiling point: 104° C.) has a lower boiling point than that of acetic acid (boiling point: 117° C.), crotonaldehyde is more concentrated in a column top of a distillation column by increasing the reflux ratio of the lower boiling point component removal column. Thereby, the crotonaldehyde concentration in the first acetic acid stream obtained as a side stream or a bottom stream is decreased. When the condensate (aqueous phase and/or organic phase) of the first overhead stream in which crotonaldehyde is concentrated by increasing the reflux ratio of the lower boiling point component removal column is recycled to the reaction vessel, crotonaldehyde reacts with acetaldehyde in the reaction vessel, to produce 2-ethyl crotonaldehyde. Crotonaldehyde reacts with hydrogen in the reaction vessel, to produce butanol, and butanol reacts with acetic acid to become butyl acetate. 2-ethyl crotonaldehyde has a smaller influence on the potassium permanganate test value than that of crotonaldehyde, and butyl acetate does not have an influence on the potassium permanganate test value at all. Therefore, the quality of acetic acid tends to be more improved. Since 2-ethyl crotonaldehyde and butyl acetate respectively have boiling points of 137° C. and 126° C. which are higher than the boiling point (117° C.) of acetic acid, 2-ethyl crotonaldehyde and butyl acetate are apt to be concentrated in a side cut below a charging mixture feeding position to the lower boiling point component removal column, and a bottom fraction by increasing the reflux ratio of the lower boiling point component removal column.

When only the aqueous phase of the condensate of the first overhead stream is refluxed to the lower boiling point component removal column, the reflux ratio of the aqueous phase (amount of aqueous phase refluxed/amount of the distillate of aqueous phase) for the reflux ratio of the lower boiling point component removal column is, for example, not less than 2, preferably not less than 3, more preferably not less than 4, further preferably not less than 8, particularly preferably not less than 10. When only the organic phase of the condensate of the first overhead stream is refluxed to the lower boiling point component removal column, the reflux ratio of the organic phase (amount of organic phase refluxed/amount of the distillate of organic phase) is, for example, not less than 1, preferably not less than 1.5, more preferably not less than 2, further preferably not less than 4, particularly preferably not less than 5. Furthermore, when both the aqueous phase and the organic phase of the condensate of the first overhead stream are refluxed to the lower boiling point component removal column, the total reflux ratio of the aqueous phase and the organic phase (total amount of aqueous phase and organic phase refluxed/total amount of the distillate of aqueous phase and organic phase) is, for example, not less than 1.5, preferably not less than 2.3, more preferably not less than 3, further preferably not less than 6, particularly preferably not less than 7.5. When the aqueous phase is refluxed to the lower boiling point component removal column, the reflux ratio of the aqueous phase (amount of aqueous phase refluxed/amount of the distillate of aqueous phase) is preferably not less than 2, more preferably not less than 3, further preferably not less than 5, particularly preferably not less than 8, especially, not less than 12. When the reflux ratio of the dehydration column is controlled to not less than 0.32 as described above, the reflux ratio of the lower boiling point component removal column may be, for example, not less than 0.5 regardless of any of an upper phase and a lower phase being refluxed. In any case, the upper limit of the reflux ratio of the lower boiling point component removal column may be, for example, 3000 (particularly, 1000) or 100 (particularly, 30).

Still another examples of the method for decreasing the crotonaldehyde concentration in the first acetic acid stream include decreasing the concentration of acetaldehyde which is present in the reaction mixture liquid (reaction medium) of the reaction vessel. Since the production of crotonaldehyde caused by the aldol condensation of acetaldehyde is suppressed by decreasing the acetaldehyde concentration in the reaction mixture liquid of the reaction vessel, the crotonaldehyde concentration in the charging mixture of the first distillation column is decreased. Therefore, the crotonaldehyde concentration in the first acetic acid stream obtained by lower boiling point component removal in the first distillation column is also decreased. The acetaldehyde concentration in the reaction mixture liquid of the reaction vessel is, for example, not more than 500 ppm by mass, preferably not more than 450 ppm by mass, more preferably not more than 400 ppm by mass, further preferably not more than 350 ppm by mass, particularly preferably not more than 300 ppm by mass (for example, not more than 250 ppm by mass). The acetaldehyde concentration in the reaction mixture liquid of the reaction vessel can be decreased by increasing a CO partial pressure in the reaction vessel or increasing the methyl acetate concentration in the reaction mixture liquid of the reaction vessel, for example. The acetaldehyde concentration in the reaction mixture liquid of the reaction vessel can be decreased by increasing the percentage of a condensate (aqueous phase and/or organic phase) of a first overhead liquid obtained in the first distillation column, to be fed to the acetaldehyde separation and removal step, and decreasing the percentage of the condensate recycled to the reaction vessel.

On the other hand, when the reflux ratio of the dehydration column is controlled to not less than 0.32, crotonaldehyde flowing into the dehydration column can be concentrated to a column top since crotonaldehyde has a lower boiling point than that of acetic acid as described above, which can remarkably decrease the crotonaldehyde concentration in the second acetic acid stream obtained as the side stream or the bottom stream. When the second overhead stream of the column top of the dehydration column in which crotonaldehyde is concentrated is recycled to the reaction vessel, crotonaldehyde is transformed into less harmful 2-ethyl crotonaldehyde and harmless butyl acetate as described above, which more improves the quality of acetic acid.

The reflux ratio of the dehydration column is preferably not less than 0.35, more preferably not less than 0.4, further preferably not less than 1, particularly preferably not less than 2. When the crotonaldehyde concentration in the first acetic acid stream is controlled to not more than 2.2 ppm by mass, the reflux ratio of the dehydration column may be, for example, not less than 0.2 (particularly, not less than 0.3). The upper limit of the reflux ratio of the dehydration column is, for example, 3000 (particularly, 1000), and may be 100 or on the order of 10.

In the present invention, a 2-ethyl crotonaldehyde concentration in the first acetic acid stream is, for example, not more than 3.0 ppm by mass, preferably not more than 2.0 ppm by mass, more preferably not more than 1.0 ppm by mass, further preferably not more than 0.8 ppm by mass (for example, not more than 0.5 ppm by mass).

A ratio ($C_{CR}/C_{ECR}$) of the crotonaldehyde concentration $C_{CR}$ (ppm by mass) to the 2-ethyl crotonaldehyde concentration $C_{ECR}$ (ppm by mass) in the first acetic acid stream is, for example, not more than 35, preferably not more than 25, more preferably not more than 20, further preferably not more than 15.

A butyl acetate concentration in the first acetic acid stream is, for example, not more than 15 ppm by mass, preferably not more than 12 ppm by mass, more preferably not more than 10 ppm by mass, further preferably not more than 8 ppm by mass.

A ratio ($C_{CR}/C_{BA}$) of the crotonaldehyde concentration $C_{CR}$ (ppm by mass) to the butyl acetate concentration $C_{BA}$ (ppm by mass) in the first acetic acid stream is, for example, not more than 2.0, preferably not more than 1.5, more preferably not more than 1.0, further preferably not more than 0.6.

In the present invention, the crotonaldehyde concentration in the second acetic acid stream is, for example, not more than 2.0 ppm by mass, preferably not more than 1.8 ppm by mass, more preferably not more than 1.5 ppm by mass, further preferably not more than 1.2 ppm by mass, particularly preferably not more than 0.7 ppm by mass (for example, not more than 0.5 ppm by mass).

The 2-ethyl crotonaldehyde concentration in the second acetic acid stream is, for example, not more than 3.0 ppm by mass, preferably not more than 2.0 ppm by mass, more preferably not more than 1.0 ppm by mass, further preferably not more than 0.8 ppm by mass (for example, not more than 0.5 ppm by mass).

A ratio ($C_{CR}/C_{ECR}$) of the crotonaldehyde concentration $C_{CR}$ (ppm by mass) to the 2-ethyl crotonaldehyde concentration $C_{ECR}$ (ppm by mass) in the second acetic acid stream is, for example, not more than 35, preferably not more than 25, more preferably not more than 20, further preferably not more than 15.

The butyl acetate concentration in the second acetic acid stream is, for example, not more than 15 ppm by mass, preferably not more than 12 ppm by mass, more preferably not more than 10 ppm by mass, further preferably not more than 8 ppm by mass.

A ratio ($C_{CR}/C_{BA}$) of the crotonaldehyde concentration $C_{CR}$ (ppm by mass) to the butyl acetate concentration $C_{BA}$ (ppm by mass) in the second acetic acid stream is, for example, not more than 2.0, preferably not more than 1.5, more preferably not more than 1.0, further preferably not more than 0.6.

Hereinafter, one embodiment of the present invention will be described. FIG. 1 is one example of an acetic acid production flow diagram (carbonylation process of a methanol method) showing one embodiment of the present invention. An acetic acid production apparatus associated with this acetic acid production flow has a reaction vessel 1, an evaporator 2, a distillation column 3, a decanter 4, a distillation column 5, a distillation column 6, an ion exchange resin column 7, a scrubber system 8, an acetaldehyde separation and removal system 9, condensers 1a, 2a, 3a, 5a, and 6a, a heat exchanger 2b, reboilers 3b, 5b, and 6b, lines 11 to 56, and a pump 57 and is configured to be capable of continuously producing acetic acid. In the method for producing acetic acid according to the present embodiment, a reaction step, an evaporation step (flash step), a first distillation step, a second distillation step, a third distillation step, and an adsorptive removal step are performed in the reaction vessel 1, the evaporator 2, the distillation column 3, the distillation column 5, the distillation column 6, and the ion exchange resin column 7, respectively. The first distillation step is also referred to as a lower boiling point component removal step, the second distillation step is also referred to as a dehydration step, and the third distillation step is also referred to as a higher boiling point component removal step. In the present invention, the steps are not limited to those described above and may exclude, for example, equipment of the distillation column 6, the ion exchange resin column 7, the acetaldehyde separation and removal system 9 (acetaldehyde removal column, etc.). As mentioned later, a product column may be disposed downstream of the ion exchange resin column 7.

The reaction vessel 1 is a unit for performing the reaction step. This reaction step is a step for continuously producing acetic acid through a reaction (methanol carbonylation reaction) represented by the chemical formula (1) given below. In a steady operation state of the acetic acid production apparatus, for example, a reaction mixture under stirring with a stirrer is present in the reaction vessel 1. The reaction mixture contains methanol and carbon monoxide which are raw materials, a metal catalyst, a co-catalyst, water, a production target acetic acid, and various by-products, and a liquid phase and a gaseous phase are in equilibrium.

$$CH_3OH + CO \rightarrow CH_3COOH \quad (1)$$

The raw materials in the reaction mixture are methanol in a liquid state and carbon monoxide in a gaseous state. Methanol is continuously fed at a predetermined flow rate to the reaction vessel 1 from a methanol reservoir (not shown) through the line 11.

Carbon monoxide is continuously fed at a predetermined flow rate to the reaction vessel 1 from a carbon monoxide reservoir (not shown) through the line 12. The carbon monoxide is not necessarily required to be pure carbon monoxide and may contain, for example, other gases such as nitrogen, hydrogen, carbon dioxide, and oxygen, in a small amount (e.g., not more than 5% by mass, preferably not more than 1% by mass).

The metal catalyst in the reaction mixture promotes the carbonylation reaction of methanol, and, for example, a rhodium catalyst or an iridium catalyst can be used. For example, a rhodium complex represented by the chemical formula $[Rh(CO)_2I_2]^-$ can be used as the rhodium catalyst. For example, an iridium complex represented by the chemical formula $[Ir(CO)_2I_2]^-$ can be used as the iridium catalyst. A metal complex catalyst is preferred as the metal catalyst. The concentration (in terms of the metal) of the catalyst in the reaction mixture is, for example, 100 to 10000 ppm by mass, preferably 200 to 5000 ppm by mass, further preferably 400 to 2000 ppm by mass, with respect to the whole liquid phase of the reaction mixture.

The co-catalyst is an iodide for assisting the action of the catalyst mentioned above, and, for example, methyl iodide or an ionic iodide is used. The methyl iodide can exhibit the effect of promoting the catalytic effect of the catalyst mentioned above. The concentration of the methyl iodide is, for example, 1 to 20% by mass with respect to the whole liquid phase of the reaction mixture. The ionic iodide is an iodide that generates iodide ions in a reaction solution (particularly, an ionic metal iodide) and can exhibit the effect of stabilizing the catalyst mentioned above and the effect of suppressing side reaction. Examples of the ionic iodide include alkali metal iodides such as lithium iodide, sodium iodide, and potassium iodide. The concentration of the ionic iodide in the reaction mixture is, for example, 1 to 25% by mass, preferably 5 to 20% by mass, with respect to the whole liquid phase of the reaction mixture. When an iridium catalyst and the like are used, for example, a ruthenium compound and an osmium compound can also be used as a co-catalyst. The total used amount of the compound is, for example, 0.1 to 30 mol (in terms of the metal), preferably 0.5 to 15 mol (in terms of the metal) with respect to 1 mol of iridium (in terms of the metal).

Water in the reaction mixture is a component necessary for generating acetic acid in the reaction mechanism of the methanol carbonylation reaction and is also a component necessary for solubilizing a water-soluble component in the reaction system. The concentration of water in the reaction mixture is, for example, 0.1 to 15% by mass, preferably 0.8 to 10% by mass, further preferably 1 to 6% by mass, particularly preferably 1.5 to 4% by mass, with respect to the whole liquid phase of the reaction mixture. The water concentration is preferably not more than 15% by mass for pursuing efficient acetic acid production by reducing energy required for the removal of water in the course of purification of acetic acid. In order to control the water concentration, water may be continuously fed at a predetermined flow rate to the reaction vessel 1.

The acetic acid in the reaction mixture includes acetic acid fed in advance into the reaction vessel 1 before operation of the acetic acid production apparatus, and acetic acid generated as a main product of the methanol carbonylation reaction. Such acetic acid can function as a solvent in the reaction system. The concentration of the acetic acid in the reaction mixture is, for example, 50 to 90% by mass, preferably 60 to 80% by mass, with respect to the whole liquid phase of the reaction mixture.

Examples of the main by-products contained in the reaction mixture include methyl acetate. This methyl acetate may be generated through the reaction between acetic acid and methanol. The concentration of the methyl acetate in the reaction mixture is, for example, 0.1 to 30% by mass, preferably 1 to 10% by mass, with respect to the whole liquid phase of the reaction mixture. Another example of the by-products contained in the reaction mixture includes hydrogen iodide. This hydrogen iodide is inevitably generated under the reaction mechanism of the methanol carbonylation reaction in the case where the catalyst or the co-catalyst as mentioned above is used. The concentration of the hydrogen iodide in the reaction mixture is, for example, 0.01 to 2% by mass with respect to the whole liquid phase of the reaction mixture.

Other examples of the by-products include hydrogen, methane, carbon dioxide, acetaldehyde, crotonaldehyde, 2-ethyl crotonaldehyde, butyl acetate, dimethyl ether, alkanes, formic acid, and propionic acid, and alkyl iodides such as ethyl iodide, propyl iodide, butyl iodide, hexyl iodide and decyl iodide.

The acetaldehyde concentration in the reaction mixture liquid is, for example, not more than 500 ppm by mass, preferably not more than 450 ppm by mass, more preferably not more than 400 ppm by mass, further preferably not more than 350 ppm by mass, particularly preferably not more than 300 ppm by mass (for example, not more than 250 ppm by mass). The lower limit of the acetaldehyde concentration in the reaction mixture liquid is, for example, 1 ppm by mass (or 10 ppm by mass).

The crotonaldehyde concentration in the reaction mixture liquid is, for example, not more than 5 ppm by mass, preferably not more than 3 ppm by mass, further preferably not more than 2 ppm by mass. The lower limit of the crotonaldehyde concentration in the reaction mixture liquid is 0 ppm, and may be, for example, 0.1 ppm by mass (or 0.2 ppm by mass). The 2-ethyl crotonaldehyde concentration in the reaction mixture liquid is, for example, not more than 5 ppm by mass, preferably not more than 3 ppm by mass, further preferably not more than 2 ppm by mass. The lower limit of the 2-ethyl crotonaldehyde concentration in the reaction mixture liquid is 0 ppm, and may be, for example, 0.1 ppm by mass or 0.2 ppm by mass.

In order to achieve the object of increasing the potassium permanganate test value of product acetic acid, as described above in the present invention, the crotonaldehyde concentration in the first acetic acid stream withdrawn from the lower boiling point component removal column is controlled to not more than a specific value, or the reflux ratio of the dehydration column is controlled to not less than a specific value. In order to decrease the crotonaldehyde concentration in the first acetic acid stream, for example, the hydrogen partial pressure of the reaction vessel is increased, or the reflux ratio in the lower boiling point component removal column is increased. When the reflux ratio of the lower boiling point component removal column or the dehydration column is increased, crotonaldehyde is concentrated in the column top of each distillation column. When the concentrated crotonaldehyde is recycled to the reaction vessel, the crotonaldehyde is hydrogenated to become butyl alcohol. Furthermore, the butyl alcohol reacts with acetic acid, to be converted into butyl acetate, which is harmless to a potassium permanganate test. When the hydrogen partial pressure of the reaction vessel is increased, crotonaldehyde in the reaction vessel is apt to be hydrogenated, and is converted into harmless butyl acetate through butyl alcohol as in the above. Therefore, in the present invention, the butyl acetate concentration in the reaction mixture liquid tends to be increased. However, the increase in the butyl acetate concentration may cause a decrease in the purity of product acetic acid. For this reason, the butyl acetate concentration in the reaction mixture liquid is preferably controlled to, for example, 0.1 to 15 ppm by mass (particularly, 1 to 12 ppm by mass, especially, 2 to 9 ppm by mass).

Also, the reaction mixture may contain a metal, such as iron, nickel, chromium, manganese, or molybdenum, generated by the corrosion of the apparatus [corroded metal (also referred to as corrosion metal)], and other metals such as cobalt, zinc, and copper. The corroded metal and other metals are also collectively referred to as a "corroded metal, etc.".

In the reaction vessel 1 where the reaction mixture as described above is present, the reaction temperature is set to, for example, 150 to 250° C. The reaction pressure as the total pressure is set to, for example, 2.0 to 3.5 MPa (absolute pressure), and the carbon monoxide partial pressure is set to, for example, 0.4 to 1.8 MPa (absolute pressure), preferably 0.6 to 1.6 MPa (absolute pressure), more preferably 0.9 to 1.4 MPa (absolute pressure).

The vapor of a gaseous phase portion in the reaction vessel 1 during apparatus operation contains, for example, carbon monoxide, hydrogen, methane, carbon dioxide, nitrogen, oxygen, methyl iodide, hydrogen iodide, water, methyl acetate, acetic acid, dimethyl ether, methanol, acetaldehyde, formic acid, and propionic acid. Hydrogen is contained in carbon monoxide used as a raw material, and is produced also in a shift reaction ($CO+H_2O \rightarrow H_2+CO_2$) occurring in the reaction vessel 1. A hydrogen partial pressure in the reaction vessel 1 is, for example, not less than 0.01 MPa (absolute pressure), preferably not less than 0.015 MPa (absolute pressure), more preferably not less than 0.02 MPa (absolute pressure), further preferably not less than 0.04 MPa (absolute pressure), particularly preferably not less than 0.06 MPa (absolute pressure) [for example, not less than 0.07 MPa (absolute pressure)]. The upper limit of the hydrogen partial pressure of the reaction vessel is, for example, 0.5 MPa (absolute pressure) [particularly, 0.2 MPa (absolute pressure)]. An excessive increase in the hydrogen partial pressure of the reaction vessel causes an increase in the amount of acetaldehyde produced and an increase in crotonaldehyde due to aldol condensation. In contrast, an excessive decrease in the hydrogen partial pressure hardly causes a reaction of crotonaldehyde→butanol. The vapor of a gaseous phase portion in the reaction vessel 1 can be withdrawn from the reaction vessel 1 through the line 13. The internal pressure of the reaction vessel 1 can be controlled by the adjustment of the amount of the vapor withdrawn, and, for example, the internal pressure of the reaction vessel 1 is kept constant. The vapor withdrawn from the reaction vessel 1 is introduced to the condenser 1a.

The condenser 1a separates the vapor from the reaction vessel 1 into a condensate portion and a gaseous portion by cooling and partial condensation. The condensate portion contains, for example, methyl iodide, hydrogen iodide, water, methyl acetate, acetic acid, dimethyl ether, methanol, acetaldehyde, formic acid, and propionic acid and is introduced to the reaction vessel 1 from the condenser 1a through the line 14 and recycled. The gaseous portion contains, for example, carbon monoxide, hydrogen, methane, carbon dioxide, nitrogen, oxygen, methyl iodide, hydrogen iodide, water, methyl acetate, acetic acid, dimethyl ether, methanol, acetaldehyde, and formic acid and is fed to the scrubber system 8 from the condenser 1a through the line 15. In the scrubber system 8, useful components (e.g., methyl iodide, water, methyl acetate, and acetic acid) are separated and recovered from the gaseous portion from the condenser 1a. In this separation and recovery, a wet method that is performed using an absorbing liquid for capturing the useful components in the gaseous portion is utilized in the present embodiment. An absorption solvent containing at least acetic acid and/or methanol is preferred as the absorbing liquid. The absorbing liquid may contain methyl acetate. For example, a condensate portion of a vapor from the distillation column 6 mentioned later can be used as the absorbing liquid. In the separation and recovery, a pressure swing adsorption method may be used. The separated and recovered useful components (e.g., methyl iodide) are introduced to the reaction vessel 1 from the scrubber system 8 through the recycle line 48 and recycled. A gas after the capturing of the useful components is discarded through the line 49. The gas discharged from the line 49 can be used as a CO source to be introduced to the bottom part of the evaporator 2 mentioned later or the residual liquid stream recycle lines 18 and 19. As for treatment in the scrubber system 8 and subsequent recycle to the reaction vessel 1 and discarding, the same holds true for gaseous portions described later that are fed to the scrubber system 8 from other condensers. For the production method of the present invention, it is preferred to have a scrubber step of separating offgas from the process into a stream rich in carbon monoxide and a stream rich in acetic acid by absorption treatment with an absorption solvent containing at least acetic acid.

In the reaction vessel 1 during apparatus operation, as mentioned above, acetic acid is continuously produced. The reaction mixture containing such acetic acid is continuously withdrawn at a predetermined flow rate from the reaction vessel 1 and introduced to the next evaporator 2 through the line 16.

The evaporator 2 is a unit for performing the evaporation step (flash step). This evaporation step is a step for separating the reaction mixture continuously introduced to the evaporator 2 through the line 16 (reaction mixture feed line), into a vapor stream (volatile phase) and a residual liquid stream (low volatile phase) by partial evaporation. The evaporation may be caused by reducing the pressure without heating the reaction mixture, or the evaporation may be caused by reducing the pressure while heating the reaction mixture. In the evaporation step, the temperature of the vapor stream is, for example, 100 to 260° C., preferably 120 to 200° C., and the temperature of the residual liquid stream is, for example, 80 to 200° C., preferably 100 to 180° C. The internal pressure of the evaporator is, for example, 50 to 1000 kPa (absolute pressure). The ratio between the vapor stream and the residual liquid stream to be separated in the evaporation step is, for example, 10/90 to 50/50 (vapor stream/residual liquid stream) in terms of a mass ratio.

The vapor generated in this step contains, for example, methyl iodide, hydrogen iodide, water, methyl acetate, acetic acid, dimethyl ether, methanol, acetaldehyde, crotonaldehyde, 2-ethyl crotonaldehyde, butyl acetate, formic acid, propionic acid, and alkyl iodides such as ethyl iodide, propyl iodide, butyl iodide, hexyl iodide, and decyl iodide, and the like, and is continuously withdrawn to the line 17 (vapor stream discharge line) from the evaporator 2. A portion of the vapor stream withdrawn from the evaporator 2 is continuously introduced to the condenser 2a, and another portion of the vapor stream is continuously introduced to the next distillation column 3 through the line 21. The acetic acid concentration of the vapor stream is, for example, 50 to 85% by mass, preferably 55 to 75% by mass. The methyl iodide concentration is, for example, 2 to 50% by mass (preferably, 5 to 30% by mass). The water concentration is, for example, 0.2 to 20% by mass (preferably, 1 to 15% by mass). The methyl acetate concentration is, for example, 0.2 to 50% by mass (preferably, 2 to 30% by mass). The crotonaldehyde concentration of the vapor stream is, for example, 0 to 5 ppm by mass, preferably 0.1 to 3 ppm by mass, further preferably 0.2 to 2 ppm by mass. The 2-ethyl crotonaldehyde concentration of the vapor stream is, for example, 0 to 3 ppm by mass, preferably 0.02 to 2 ppm by mass, further preferably 0.03 to 0.8 ppm by mass. The butyl acetate concentration of the vapor stream is, for example, 0.1 to 13 ppm by mass, preferably 0.2 to 12 ppm by mass, further preferably 0.3 to 9 ppm by mass.

The residual liquid stream generated in this step contains, for example, the catalyst and the co-catalyst (methyl iodide, lithium iodide, etc.) contained in the reaction mixture, and water, methyl acetate, acetic acid, crotonaldehyde, 2-ethyl crotonaldehyde, butyl acetate, formic acid, and propionic acid remaining without being volatilized in this step, and is continuously introduced to the heat exchanger 2b from the evaporator 2 through the line 18 using the pump 57. The heat exchanger 2b cools the residual liquid stream from the evaporator 2. The cooled residual liquid stream is continuously introduced to the reaction vessel 1 from the heat exchanger 2b through the line 19 and recycled. The line 18 and the line 19 are collectively referred to as residual liquid stream recycle lines. The acetic acid concentration of the residual liquid stream is, for example, 55 to 90% by mass, preferably 60 to 85% by mass.

The condenser 2a separates the vapor stream from the evaporator 2 into a condensate portion and a gaseous portion by cooling and partial condensation. The condensate portion contains, for example, methyl iodide, hydrogen iodide, water, methyl acetate, acetic acid, dimethyl ether, methanol, acetaldehyde, crotonaldehyde, 2-ethyl crotonaldehyde, butyl acetate, formic acid, and propionic acid and is introduced to the reaction vessel 1 from the condenser 2a through the lines 22 and 23 and recycled. The gaseous portion contains, for example, carbon monoxide, hydrogen, methane, carbon dioxide, nitrogen, oxygen, methyl iodide, hydrogen iodide, water, methyl acetate, acetic acid, dimethyl ether, methanol, acetaldehyde, and formic acid and is fed to the scrubber system 8 from the condenser 2a through the lines 20 and 15. Since the reaction to produce acetic acid in the reaction step mentioned above is an exothermic reaction, a portion of heat accumulated in the reaction mixture is transferred to the vapor generated from the reaction mixture in the evaporation step (flash step). The condensate portion generated by the cooling of this vapor in the condenser 2a is recycled to the reaction vessel 1. Specifically, in this acetic acid production apparatus, heat generated through the methanol carbonylation reaction is efficiently removed in the condenser 2a.

The distillation column 3 is a unit for performing the first distillation step and serves as the so-called lower boiling point component removal column in the present embodiment. The first distillation step is the step of subjecting the vapor stream continuously introduced to the distillation column 3 to distillation treatment to separate and remove lower boiling point components. More specifically, in the first distillation step, the vapor stream is separated by distillation into an overhead stream rich in at least one lower boiling point component selected from methyl iodide and acetaldehyde, and an acetic acid stream rich in acetic acid. The distillation column 3 consists of, for example, a distillation column such as a plate column or a packed column. In the case of adopting a plate column as the distillation column 3, the theoretical number of plates thereof is, for example, 5 to 50.

In the inside of the distillation column 3, the column top pressure is set to, for example, 80 to 160 kPa (gauge pressure), and the column bottom pressure is higher than the column top pressure and is set to, for example, 85 to 180 kPa (gauge pressure). In the inside of the distillation column 3, the column top temperature is, for example, a temperature of lower than the boiling point of acetic acid at the set column top pressure and is set to 90 to 130° C., and the column bottom temperature is, for example, a temperature of not less than the boiling point of acetic acid at the set column bottom pressure and is set to 120 to 165° C. (preferably 125 to 160° C.)

The vapor stream from the evaporator 2 is continuously introduced to the distillation column 3 through the line 21. From the column top of the distillation column 3, a vapor as the overhead stream is continuously withdrawn to the line 24. From the column bottom of the distillation column 3, a bottom fraction is continuously withdrawn to the line 25. 3b denotes a reboiler. From the height position between the column top and the column bottom of the distillation column 3, the acetic acid stream (first acetic acid stream; liquid) as a side stream is continuously withdrawn through the line 27.

The vapor withdrawn from the column top of the distillation column 3 contains a larger amount of components having a lower boiling point (lower boiling point components) than that of acetic acid as compared with the bottom fraction and the side stream from the distillation column 3 and contains, for example, methyl iodide, hydrogen iodide, water, methyl acetate, dimethyl ether, methanol, acetaldehyde, crotonaldehyde, and formic acid. This vapor also contains acetic acid. Such a vapor is continuously introduced to the condenser 3a through the line 24.

The condenser 3a separates the vapor from the distillation column 3 into a condensate portion and a gaseous portion by cooling and partial condensation. The condensate portion contains, for example, methyl iodide, hydrogen iodide, water, methyl acetate, acetic acid, dimethyl ether, methanol, acetaldehyde, crotonaldehyde, and formic acid and is continuously introduced to the decanter 4 from the condenser 3a through the line 28. The condensate portion introduced to the decanter 4 is separated into an aqueous phase (upper phase) and an organic phase (methyl iodide phase; lower phase). The aqueous phase contains water and, for example, methyl iodide, hydrogen iodide, methyl acetate, acetic acid, dimethyl ether, methanol, acetaldehyde, crotonaldehyde, and formic acid. The organic phase contains, for example, methyl iodide and, for example, hydrogen iodide, water, methyl acetate, acetic acid, dimethyl ether, methanol, acetaldehyde, crotonaldehyde, and formic acid and the like. In the present embodiment, a portion of the aqueous phase is refluxed to the distillation column 3 through the line 29, and another portion of the aqueous phase is introduced to the acetaldehyde separation and removal system 9 through the lines 29, 30, and 51. Acetaldehyde is separated and removed out of the system from the line 53. A residual liquid after acetaldehyde is separated and removed is recycled to the reaction vessel 1 through the lines 52 and 23. Still another portion of the aqueous phase may be recycled to the reaction vessel 1 through the lines 29, 30, and 23 without passing through the acetaldehyde separation and removal system 9. The organic phase is introduced into the reaction vessel 1 through the lines 31 and 23, and is recycled. A portion of the organic phase may be introduced into the acetaldehyde separation and removal system 9 through the lines 31 and 50 as necessary. In addition to, or instead of the reflux of the aqueous phase to the distillation column 3, the organic phase may be refluxed to the distillation column 3.

The reflux ratio of the distillation column 3 will be described later. When only the aqueous phase of a condensate portion of an overhead stream (first overhead stream) is refluxed to the distillation column 3, it is desirable that the reflux ratio of the aqueous phase (amount of aqueous phase refluxed/amount of the distillate of aqueous phase) be, for example, not less than 2, preferably not less than 3, more preferably not less than 4, further preferably not less than 8, particularly preferably not less than 10. When only the organic phase of the condensate portion of the overhead stream is refluxed to the distillation column 3, it is desirable that the reflux ratio of the organic phase (amount of organic phase refluxed/amount of the distillate of organic phase) be, for example, not less than 1, preferably not less than 1.5, more preferably not less than 2, further preferably not less than 4, particularly preferably not less than 5. Furthermore, when both the aqueous phase and the organic phase of the condensate portion of the overhead stream are refluxed to the distillation column 3, it is desirable that the total reflux ratio of the aqueous phase and the organic phase (total amount of aqueous phase and organic phase refluxed/total amount of the distillate of aqueous phase and organic phase) be, for example, not less than 1.5, preferably not less than 2.3, more preferably not less than 3, further preferably not less than 6, particularly preferably not less than 7.5. When the aqueous phase is refluxed to the distillation column 3, the reflux ratio of the aqueous phase (amount of aqueous phase refluxed/amount of the distillate of aqueous phase) is preferably not less than 2, more preferably not less than 3, further preferably not less than 5, particularly preferably not less than 8, especially, not less than 12. When the reflux ratio of a distillation column 5 to be described later is controlled to not less than 0.32, the reflux ratio of the distillation column 3 may be, for example, not less than 0.5 regardless of any of an upper phase and a lower phase being refluxed. In any case, the upper limit of the reflux ratio of the distillation column 3 may be, for example, 3000 (particularly, 1000) or may be 100 (particularly, 30). Since crotonaldehyde (boiling point: 104° C.) has a lower boiling point than that of acetic acid (boiling point: 117° C.), crotonaldehyde is more concentrated to the column top of the distillation column 3 by increasing the reflux ratio of the distillation column 3, which causes a decrease in the crotonaldehyde concentration in the first acetic acid stream obtained as a side stream, for example. When the condensate portion (aqueous phase and/or organic phase) of the first overhead stream in which crotonaldehyde is concentrated is recycled to the reaction vessel 1 by increasing the reflux ratio of the distillation column 3, crotonaldehyde reacts with acetaldehyde in the reaction vessel 1, to produce 2-ethyl crotonaldehyde. Crotonaldehyde reacts with hydrogen in the reaction vessel 1 to produce butanol, and the butanol reacts with acetic acid to become butyl acetate. 2-ethyl crotonaldehyde has a smaller influence on the potassium permanganate test value than that of crotonaldehyde, and butyl acetate does not have an influence on the potassium permanganate test value at all. Therefore, the quality of acetic acid tends to be more improved. Since 2-ethyl crotonaldehyde and butyl acetate respectively have boiling points of 137° C. and 126° C. which are higher than the boiling point (117° C.) of acetic acid, 2-ethyl crotonaldehyde and butyl acetate are apt to be concentrated in a side cut below a charging mixture feeding position to the distillation column 3, and a bottom fraction by increasing the reflux ratio of the distillation column 3.

In the acetaldehyde separation and removal step using the acetaldehyde separation and removal system 9, acetaldehyde contained in the organic phase and/or the aqueous phase is separated and removed by a method known in the art, for example, distillation, extraction, or a combination thereof. The separated acetaldehyde is discharge to the outside of the apparatus through the line 53. The useful components (e.g., methyl iodide) contained in the organic phase and/or the aqueous phase are recycled to the reaction vessel 1 through the lines 52 and 23 and reused.

FIG. 2 is a schematic flow diagram showing one example of the acetaldehyde separation and removal system. According to this flow, in the case of treating, for example, the organic phase in the acetaldehyde separation and removal step, the organic phase is fed to a distillation column (first acetaldehyde removal column) 91 through a line 101 and separated by distillation into an overhead stream rich in acetaldehyde (line 102) and a residual liquid stream rich in methyl iodide (line 103). The overhead stream is condensed in a condenser 91a. A portion of the condensate is refluxed to the column top of the distillation column 91 (line 104), and the remaining portion of the condensate is fed to an extraction column 92 (line 105). The condensate fed to the extraction column 92 is subjected to extraction treatment with water introduced from a line 109. The extract obtained by the extraction treatment is fed to a distillation column (second acetaldehyde removal column) 93 through a line 107 and separated by distillation into an overhead stream rich in acetaldehyde (line 112) and a residual liquid stream rich in water (line 113). Then, the overhead stream rich in acetaldehyde is condensed in a condenser 93a. A portion of the condensate is refluxed to the column top of the distillation column 93 (line 114), and the remaining portion of the condensate is discharged to the outside of the system (line 115). The residual liquid stream rich in methyl iodide, which is a bottom fraction of the first acetaldehyde removal column 91, a raffinate rich in methyl iodide (line 108) obtained in the extraction column 92, and the residual liquid stream rich in water, which is a bottom fraction of the second acetaldehyde removal column 93 are recycled to the reaction vessel 1 through the lines 103, 111, and 113, respectively, or recycled to an appropriate area of the process and reused. For example, the raffinate rich in methyl iodide, obtained in the extraction column 92, can be recycled to the distillation column 91 through a line 110. The liquid from the line 113 is usually discharged to the outside as water discharge. A gas that has not been condensed in the condenser 91a or 93a (line 106 or 116) is subjected to absorption treatment in the scrubber system 8 or discarded.

According to the flow of FIG. 2, in the case of treating the aqueous phase in the acetaldehyde separation and removal step, for example, the aqueous phase is fed to the distillation column (first acetaldehyde removal column) 91 through the line 101 and separated by distillation into an overhead stream rich in acetaldehyde (line 102) and a residual liquid stream rich in water (line 103). The overhead stream is condensed in the condenser 91a. A portion of the condensate is refluxed to the column top of the distillation column 91 (line 104), and the remaining portion of the condensate is fed to the extraction column 92 (line 105). The condensate fed to the extraction column 92 is subjected to extraction treatment with water introduced from the line 109. The extract obtained by the extraction treatment is fed to the distillation column (second acetaldehyde removal column) 93 through the line 107 and separated by distillation into an overhead stream rich in acetaldehyde (line 112) and a residual liquid stream rich in water (line 113). Then, the overhead stream rich in acetaldehyde is condensed in the condenser 93a. A portion of the condensate is refluxed to the column top of the distillation column 93 (line 114), and the remaining portion of the condensate is discharged to the outside of the system (line 115). The residual liquid stream rich in water, which is a bottom fraction of the first acetaldehyde removal column 91, a raffinate rich in methyl iodide (line 108) obtained in the extraction column 92, and the residual liquid stream rich in water, which is a bottom fraction of the second acetaldehyde removal column 93 are recycled to the reaction vessel 1 through the lines 103, 111, and 113, respectively, or recycled to an appropriate area of the process and reused. For example, the raffinate rich in methyl iodide, obtained in the extraction column 92, can be recycled to the distillation column 91 through the line 110. The liquid from the line 113 is usually discharged to the outside as water discharge. A gas that has not been condensed in the condenser 91a or 93a (line 106 or 116) is subjected to absorption treatment in the scrubber system 8 or discarded.

The acetaldehyde derived from the process stream containing at least the water, the acetic acid (AC), the methyl iodide (MeI), and the acetaldehyde (AD) can also be separated and removed by use of extractive distillation, in addition to the method described above. For example, the organic phase and/or the aqueous phase (charging mixture) obtained by the separation of the process stream is fed to a distillation column (extractive distillation column). In addition, an extraction solvent (usually, water) is introduced to a concentration zone (e.g., space from the column top to the charging mixture feeding position) where methyl iodide and acetaldehyde in the distillation column are concentrated. A liquid (extract) dropped from the concentration zone is withdrawn as a side stream (side cut stream). This side stream is separated into an aqueous phase and an organic phase. The aqueous phase can be distilled to thereby discharge acetaldehyde to the outside of the system. In the case where a relatively large amount of water is present in the distillation column, the liquid dropped from the concentration zone may be withdrawn as a side stream without introducing the extraction solvent to the distillation column. For example, a unit (chimney tray, etc.) that can receive the liquid (extract) dropped from the concentration zone is disposed in this distillation column so that a liquid (extract) received by this unit can be withdrawn as a side stream. The extraction solvent introduction position is preferably superior to the charging mixture feeding position, more preferably near the column top. The side stream withdrawal position is preferably lower than the extraction solvent introduction position and higher than the charging mixture feeding position, in the height direction of the column. According to this method, acetaldehyde can be extracted with a high concentration from a concentrate of methyl iodide and the acetaldehyde using an extraction solvent (usually, water). In addition, the region between the extraction solvent introduction site and the side cut site is used as an extraction zone. Therefore, acetaldehyde can be efficiently extracted with a small amount of the extraction solvent. Therefore, for example, the number of plates in the distillation column can be drastically decreased as compared with a method of withdrawing an extract by extractive distillation from the column bottom of the distillation column (extractive distillation column). In addition, steam load can also be reduced. Furthermore, the ratio of methyl iodide to acetaldehyde (MeI/AD ratio) in a water extract can be decreased as compared with a method of combining the aldehyde removing distillation of FIG. 2 with water extraction using a small amount of an extraction solvent. Therefore, acetaldehyde can be removed under conditions that can suppress a loss of methyl iodide to the outside of the system. The acetaldehyde concentration in the side stream is much higher than the acetaldehyde concentration in the charging mixture and the bottom fraction (column bottom fraction). The ratio of acetaldehyde to methyl iodide in the side stream is larger than the ratio of acetaldehyde to methyl iodide in the charging mixture and the bottom fraction. The organic phase (methyl iodide phase) obtained by the separation of the side stream may be recycled to this distillation column. In this case, the recycle position of the organic phase obtained by the separation of the side stream is preferably lower than the side stream withdrawal position and preferably higher than the charging mixture feeding position, in the height direction of the column. A solvent miscible with the components (e.g., methyl acetate) constituting the organic phase obtained by the separation of the process stream may be introduced to this distillation column (extractive distillation column). Examples of the miscible solvent include acetic acid and ethyl acetate. The miscible solvent introduction position is preferably lower than the side stream withdrawal position and preferably higher than the charging mixture feeding position, in the height direction of the column. Also, the miscible solvent introduction position is preferably inferior to a recycle position in the case where the organic phase obtained by the separation of the side stream is recycled to this distillation column. The organic phase obtained by the separation of the side stream is recycled to the distillation column, or the miscible solvent is introduced to the distillation column, whereby the methyl acetate concentration in the extract withdrawn as the side stream can be decreased, and the methyl acetate concentration in the aqueous phase obtained by the separation of the extract can be lowered. Hence, the contamination of the aqueous phase with methyl iodide can be suppressed.

The theoretical number of plates of the distillation column (extractive distillation column) is, for example, 1 to 100, preferably 2 to 50, further preferably 3 to 30, particularly preferably 5 to 20. Acetaldehyde can be efficiently separated and removed by a smaller number of plates than 80 to 100 plates in a distillation column or an extractive distillation column for use in conventional acetaldehyde removal. The mass ratio between the flow rate of the extraction solvent and the flow rate of the charging mixture (the organic phase and/or the aqueous phase obtained by the separation of the process stream) (former/latter) may be selected from the range of 0.0001/100 to 100/100 and is usually 0.0001/100 to 20/100, preferably 0.001/100 to 10/100, more preferably 0.01/100 to 8/100, further preferably 0.1/100 to 5/100. The column top temperature of the distillation column (extractive distillation column) is, for example, 15 to 120° C., preferably 20 to 90° C., more preferably 20 to 80° C., further preferably 25 to 70° C. The column top pressure is, on the order of, for example, 0.1 to 0.5 MPa in terms of absolute pressure. Other conditions for the distillation column (extractive distillation column) may be the same as those for a distillation column or an extractive distillation column for use in conventional acetaldehyde removal.

FIG. 3 is a schematic flow diagram showing another example of the acetaldehyde separation and removal system using the extractive distillation described above. In this example, the organic phase and/or the aqueous phase (charging mixture) obtained by the separation of the process stream is fed to a middle part (position between the column top and the column bottom) of a distillation column 94 through a feed line 201, while water is introduced thereto from near the column top through a line 202 so that extractive distillation is performed in the distillation column 94 (extractive distillation column). A chimney tray 200 for receiving a liquid (extract) dropped from a concentration zone where methyl iodide and acetaldehyde in the column are concentrated is disposed superior to the charging mixture feeding position of the distillation column 94. In this extractive distillation, preferably the whole amount, of the liquid on the chimney tray 200 is withdrawn, introduced to a decanter 95 through a line 208, and separated. The aqueous phase (containing acetaldehyde) in the decanter 95 is introduced to a cooler 95a through a line 212 and cooled so that methyl iodide dissolved in the aqueous phase is separated into 2 phases in a decanter 96. The aqueous phase in the decanter 96 is fed to a distillation column 97 (acetaldehyde removal column) through a line 216 and distilled. The vapor at the column top is led to a condenser 97a through a line 217 and condensed. A portion of the condensate (mainly, acetaldehyde and methyl iodide) is refluxed to the column top of the distillation column 97, and the remaining portion is discarded or fed to a distillation column 98 (extractive distillation column) through a line 220. Water is introduced thereto from near the column top of the distillation column 98 through a line 222, followed by extractive distillation. The vapor at the column top is led to a condenser 98a through a line 223 and condensed. A portion of the condensate (mainly, methyl iodide) is refluxed to the column top, and the remaining portion is recycled to the reaction system through a line 226, but may be discharged to the outside of the system. Preferably the whole amount, of the organic phase (methyl iodide phase) in the decanter 95 is recycled to below the position of the chimney tray 200 of the distillation column 94 through lines 209 and 210. A portion of the aqueous phase of the decanter 95 and the organic phase of the decanter 96 are recycled to the distillation column 94 through lines 213 and 210 and lines 214 and 210, respectively, but may not be recycled. A portion of the aqueous phase of the decanter 95 may be utilized as an extraction solvent (water) in the distillation column 94. A portion of the aqueous phase of the decanter 96 may be recycled to the distillation column 94 through the line 210. In some cases (e.g., the case where methyl acetate is contained in the charging mixture), a solvent (acetic acid, ethyl acetate, etc.) miscible with the components (e.g., methyl acetate) constituting the organic phase obtained by the separation of the process stream may be fed to the distillation column 94 through a line 215 to thereby improve distillation efficiency. The feeding position of the miscible solvent to the distillation column 94 is superior to the charging mixture feeding portion (junction of the line 201) and inferior to the junction of the recycle line 210. A bottom fraction of the distillation column 94 is recycled to the reaction system. A vapor at the column top of the distillation column 94 is led to a condenser 94a through a line 203 and condensed. The condensate is separated in a decanter 99. The organic phase is refluxed to the column top of the distillation column 94 through a line 206, while the aqueous phase is led to the decanter 95 through a line 207. A bottom fraction (water is a main component) of the distillation column 97 and a bottom fraction (water containing a small amount of acetaldehyde) of the distillation column 98 (extractive distillation column) are discharged to the outside of the system through lines 218 and 224, respectively, or recycled to the reaction system. A gas that has not been condensed in the condenser 94a, 97a, or 98a (line 211, 221, or 227) is subjected to absorption treatment in the scrubber system 8, or discarded.

FIG. 4 is a schematic flow diagram showing a further alternative example of the acetaldehyde separation and removal system using the extractive distillation described above. In this example, a condensate of a vapor from the column top of the distillation column 94 is led to a hold tank 100, and the whole amount thereof is refluxed to the column top of the distillation column 94 through the line 206. The other points are the same as in the example of FIG. 3.

FIG. 5 is a schematic flow diagram showing a further alternative example of the acetaldehyde separation and removal system using the extractive distillation described above. In this example, the whole amount of a liquid on the chimney tray 200 is withdrawn, directly introduced to the cooler 95a through the line 208 without the medium of the decanter 95, cooled, and fed to the decanter 96. The other points are the same as in the example of FIG. 4.

In FIG. 1 described above, the gaseous portion generated in the condenser 3a contains, for example, carbon monoxide, hydrogen, methane, carbon dioxide, nitrogen, oxygen, methyl iodide, hydrogen iodide, water, methyl acetate, acetic acid, dimethyl ether, methanol, acetaldehyde, and formic acid and is fed to the scrubber system 8 from the condenser 3a through the lines 32 and 15. For example, methyl iodide, hydrogen iodide, water, methyl acetate, acetic acid, dimethyl ether, methanol, acetaldehyde, and formic acid in the gaseous portion that has entered the scrubber system 8 are absorbed to an absorbing liquid in the scrubber system 8. The hydrogen iodide generates methyl iodide through reaction with methanol or methyl acetate in the absorbing liquid. Then, a liquid portion containing useful components such as the methyl iodide is recycled to the reaction vessel 1 from the scrubber system 8 through the recycle lines 48 and 23 and reused.

The bottom fraction withdrawn from the column bottom of the distillation column 3 contains a larger amount of components having a higher boiling point (higher boiling point components) than that of acetic acid as compared with the overhead stream and the side stream from the distillation column 3 and contains, for example, propionic acid, and the entrained catalyst and co-catalyst mentioned above. This bottom fraction also contains, for example, acetic acid, methyl iodide, methyl acetate, 2-ethyl crotonaldehyde, butyl acetate, and water. In the present embodiment, a portion of such a bottom fraction is continuously introduced to the evaporator 2 through the lines 25 and 26 and recycled, and another portion of the bottom fraction is continuously introduced to the reaction vessel 1 through the lines 25 and 23 and recycled.

The first acetic acid stream continuously withdrawn as a side stream from the distillation column 3 is more enriched with acetic acid than the vapor stream continuously introduced to the distillation column 3. Specifically, the acetic acid concentration of the first acetic acid stream is higher than the acetic acid concentration of the vapor stream. The acetic acid concentration of the first acetic acid stream is, for example, 90 to 99.9% by mass, preferably 93 to 99% by mass. The first acetic acid stream contains, in addition to acetic acid, for example, methyl iodide, hydrogen iodide, water, methyl acetate, dimethyl ether, methanol, acetaldehyde, crotonaldehyde, 2-ethyl crotonaldehyde, butyl acetate, formic acid, propionic acid, and alkyl iodides such as ethyl iodide, propyl iodide, butyl iodide, hexyl iodide, and decyl iodide, and the like. In the first acetic acid stream, a methyl iodide concentration is, for example, 0.1 to 8% by mass, preferably 0.2 to 5% by mass; a water concentration is, for example, 0.1 to 8% by mass, preferably 0.2 to 5% by mass; and a methyl acetate concentration is, for example, 0.1 to 8% by mass, preferably 0.2 to 5% by mass.

In the present invention, the crotonaldehyde concentration in the first acetic acid stream is controlled to not more than 2.2 ppm by mass. This can decrease the crotonaldehyde concentration in the second acetic acid stream obtained by separating and removing water in the dehydration step, and can increase the potassium permanganate test value of the second acetic acid stream. For this reason, acetaldehyde removal equipment and ozonation equipment which have been conventionally used for an increase in the potassium permanganate test value can be made small-scale, or omitted. Since acetic acid having a high potassium permanganate test value can be obtained through only the lower boiling point component removal column and the dehydration column, a subsequent higher boiling point component removal column and a product column (finishing column) can be made small-scale, or omitted. The crotonaldehyde concentration in the first acetic acid stream is preferably not more than 2.0 ppm by mass, more preferably not more than 1.8 ppm by mass, further preferably not more than 1.5 ppm by mass, particularly preferably not more than 1.2 ppm by mass (for example, not more than 1.0 ppm by mass, or not more than 0.8 ppm by mass, among others, not more than 0.5 ppm by mass). When the reflux ratio of the distillation column 5 to be described later is controlled to not less than 0.32, the crotonaldehyde concentration in the first acetic acid stream is not limited to the above. The crotonaldehyde concentration may be, for example, not more than 5 ppm by mass (particularly, not more than 2.5 ppm by mass), and is preferably within the ranges described above.

The 2-ethyl crotonaldehyde concentration in the first acetic acid stream is, for example, not more than 3.0 ppm by mass, preferably not more than 2.0 ppm by mass, more preferably not more than 1.0 ppm by mass, further preferably not more than 0.8 ppm by mass (for example, not more than 0.5 ppm by mass). A ratio ($C_{CR}/C_{ECR}$) of the crotonaldehyde concentration $C_{CR}$ (ppm by mass) to the 2-ethyl crotonaldehyde concentration $C_{ECR}$ (ppm by mass) in the first acetic acid stream is, for example, not more than 35, preferably not more than 25, more preferably not more than 20, further preferably not more than 15. Since crotonaldehyde has a greater negative influence on a potassium permanganate test value than that of 2-ethyl crotonaldehyde, the potassium permanganate test value of product acetic acid tends to be increased as the ratio ($C_{CR}/C_{ECR}$) is smaller.

The butyl acetate concentration in the first acetic acid stream is, for example, not more than 15 ppm by mass, preferably not more than 12 ppm by mass, more preferably not more than 10 ppm by mass, further preferably not more than 8 ppm by mass. The lower limit of the butyl acetate concentration in the first acetic acid stream is, for example, 0 ppm by mass (or 0.1 ppm by mass). A ratio ($C_{CR}/C_{BA}$) of the crotonaldehyde concentration $C_{CR}$ (ppm by mass) to the butyl acetate concentration $C_{BA}$ (ppm by mass) in the first acetic acid stream is, for example, not more than 2.0, preferably not more than 1.5, more preferably not more than 1.0, further preferably not more than 0.6. Since butyl acetate is harmless to the potassium permanganate test, the potassium permanganate test value of product acetic acid tends to be increased as the ratio ($C_{CR}/C_{BA}$) is smaller.

The connection position of the line 27 to the distillation column 3 may be, as shown in the drawing, higher than the connection position of the line 21 to the distillation column 3 in the height direction of the distillation column 3, but may be lower than the connection position of the line 21 to the distillation column 3 or may be the same as the connection position of the line 21 to the distillation column 3. The first acetic acid stream from the distillation column 3 is continuously introduced at a predetermined flow rate to the next distillation column 5 through the line 27. The line 27 and the distillation column 5 (at least a liquid contact part and gas contact part) may be made of stainless steel, and is preferably made of a high corrosion resistant metal such as a nickel base alloy or zirconium in order to suppress the internal corrosion of the line caused by hydrogen iodide or acetic acid.

To the first acetic acid stream flowing through the line 27, potassium hydroxide can be fed or added through the line 55 (potassium hydroxide introduction line). The potassium hydroxide can be fed or added, for example, as a solution such as an aqueous solution. Hydrogen iodide in the first acetic acid stream can be decreased by the feed or addition of potassium hydroxide to the first acetic acid stream. Specifically, the hydrogen iodide reacts with the potassium hydroxide to form potassium iodide and water. This can reduce the corrosion of an apparatus such as a distillation column ascribable to hydrogen iodide. In this process, the potassium hydroxide can be fed or added to an appropriate site where hydrogen iodide is present. The potassium hydroxide added during the process also reacts with acetic acid to form potassium acetate.

The distillation column 5 is a unit for performing the second distillation step and serves as the so-called dehydration column in the present embodiment. The second distillation step is a step for further purifying acetic acid by the distillation treatment of the first acetic acid stream continuously introduced to the distillation column 5. The distillation column 5 (at least a liquid contact part and gas contact part) is preferably made of a nickel base alloy or zirconium. The use of such a material can suppress the internal corrosion of the distillation column caused by hydrogen iodide or acetic acid, to allow the elution of corroded metal ions to be suppressed.

The charging mixture of the distillation column 5 contains at least a portion (line 27) of the first acetic acid stream, and a stream other than the first acetic acid stream [for example, a recycle stream from a downstream step (for example, a line 42)] may be added to the charging mixture.

The distillation column 5 consists of, for example, a distillation column such as a plate column or a packed column. In the case of adopting a plate column as the distillation column 5, the theoretical number of plates thereof is, for example, 5 to 50. In the present invention, the reflux ratio of the distillation column 5 is controlled to not less than 0.32. When the reflux ratio of the distillation column 5 is controlled to not less than 0.32, crotonaldehyde flowing into the dehydration column can be concentrated to the column top since crotonaldehyde has a lower boiling point than that of acetic acid, which can remarkably decrease the crotonaldehyde concentration in the second acetic acid stream obtained as the side stream or the bottom stream. When the overhead stream (second overhead stream) of the column top of the distillation column 5 in which crotonaldehyde is concentrated is recycled to the reaction vessel 1, crotonaldehyde is transformed into 2-ethyl crotonaldehyde which is less harmful to the potassium permanganate test value and butyl acetate which is harmless thereto, as described above, which provides a more improvement in the quality of acetic acid.

The reflux ratio of the distillation column 5 is preferably not less than 0.35, more preferably not less than 0.4, further preferably not less than 1, particularly preferably not less than 2. When the crotonaldehyde concentration in the first acetic acid stream is controlled to not more than 2.2 ppm by mass, the reflux ratio of the distillation column 5 may be, for example, not less than 0.2 (particularly, not less than 0.3). The upper limit of the reflux ratio of the distillation column 5 is, for example, 3000 (particularly, 1000), and may be 100 or on the order of 10.

In the inside of the distillation column 5 in the second distillation step, the column top pressure is, for example, 0.10 to 0.28 MPa (gage pressure), preferably 0.15 to 0.23 MPa (gage pressure), further preferably 0.17 to 0.21 MPa (gage pressure). The column bottom pressure is higher than the column top pressure and is, for example, 0.13 to 0.31 MPa (gage pressure), preferably 0.18 to 0.26 MPa (gage pressure), further preferably 0.20 to 0.24 MPa (gage pressure). In the inside of the distillation column 5 in the second distillation step, it is preferable that the column top temperature be less than 165° C. and the column bottom temperature be less than 175° C. By setting the column top temperature and the column bottom temperature of the distillation column 5 to the above ranges, the internal corrosion of the distillation column caused by hydrogen iodide or acetic acid is more suppressed to allow the elution of corroded metal ions to be more suppressed. The column top temperature is more preferably less than 163° C., further preferably less than 161° C., particularly preferably less than 160° C., especially preferably, less than 155° C. The lower limit of the column top temperature is, for example, 110° C. The column bottom temperature is more preferably less than 173° C., further preferably less than 171° C., particularly preferably less than 166° C. The lower limit of the column bottom temperature is, for example, 120° C.

A vapor as an overhead stream (the second overhead stream) is continuously withdrawn to the line 33 from the column top of the distillation column 5. A bottom fraction is continuously withdrawn to the line 34 from the column bottom of the distillation column 5. 5b denotes a reboiler. A side stream (liquid or gas) may be continuously withdrawn to the line 34 from the height position between the column top and the column bottom of the distillation column 5.

The vapor withdrawn from the column top of the distillation column 5 contains a larger amount of components having a lower boiling point (lower boiling point components) than that of acetic acid as compared with the bottom fraction from the distillation column 5 and contains, for example, methyl iodide, hydrogen iodide, water, methyl acetate, acetic acid, dimethyl ether, methanol, acetaldehyde, crotonaldehyde, and formic acid. Such a vapor is continuously introduced to the condenser 5a through the line 33.

The condenser 5a separates the vapor from the distillation column 5 into a condensate portion and a gaseous portion by cooling and partial condensation. The condensate portion contains, for example, water and acetic acid. A portion of the condensate portion is continuously refluxed to the distillation column 5 from the condenser 5a through the line 35. Another portion of the condensate portion is continuously introduced to the reaction vessel 1 from the condenser 5a through the lines 35, 36, and 23 and recycled. The gaseous portion generated in the condenser 5a contains, for example, carbon monoxide, hydrogen, methane, carbon dioxide, nitrogen, oxygen, methyl iodide, hydrogen iodide, water, methyl acetate, acetic acid, dimethyl ether, methanol, acetaldehyde, and formic acid and is fed to the scrubber system 8 from the condenser 5a through the lines 37 and 15. Hydrogen iodide in the gaseous portion that has entered the scrubber system 8 is absorbed to an absorbing liquid in the scrubber system 8. Methyl iodide is generated through the reaction of the hydrogen iodide with methanol or methyl acetate in the absorbing liquid. Then, a liquid portion containing useful components such as the methyl iodide is recycled to the reaction vessel 1 from the scrubber system 8 through the recycle lines 48 and 23 and reused.

The bottom fraction withdrawn from the column bottom of the distillation column 5 or the side stream (second acetic acid stream) withdrawn from the intermediate position of the column is more enriched with acetic acid than the first acetic acid stream continuously introduced to the distillation column 5. Specifically, the acetic acid concentration of the second acetic acid stream is higher than the acetic acid concentration of the first acetic acid stream. The acetic acid concentration of the second acetic acid stream is, for example, 99.1 to 99.99% by mass as long as being higher than the acetic acid concentration of the first acetic acid stream. In the present embodiment, in the case of withdrawing a side stream, the withdrawal position of the side stream from the distillation column 5 is lower than the introduction position of the first acetic acid stream to the distillation column 5 in the height direction of the distillation column 5.

Since the second acetic acid stream has a high potassium permanganate test value in the present invention, the second acetic acid stream can be used as product acetic acid as it is. However, the second acetic acid stream may contain a very small amount of impurities [for example, crotonaldehyde, 2-ethyl crotonaldehyde, butyl acetate, propionic acid, potassium acetate (in the case of feeding potassium hydroxide to the line 27 etc.), hydrogen iodide, and the entrained catalyst and co-catalyst mentioned above]. Therefore, the bottom fraction or the side stream may be continuously introduced to the distillation column 6 through the line 34 and distilled.

The crotonaldehyde concentration in the second acetic acid stream is, for example, not more than 2.0 ppm by mass, preferably not more than 1.8 ppm by mass, more preferably not more than 1.5 ppm by mass, further preferably not more than 1.2 ppm by mass, particularly preferably not more than 0.7 ppm by mass (for example, not more than 0.5 ppm by mass). The 2-ethyl crotonaldehyde concentration in the second acetic acid stream is, for example, not more than 3.0 ppm by mass, preferably not more than 2.0 ppm by mass, more preferably not more than 1.0 ppm by mass, further preferably not more than 0.8 ppm by mass (for example, not more than 0.5 ppm by mass). A ratio ($C_{CR}/C_{ECR}$) of the crotonaldehyde concentration $C_{CR}$ (ppm by mass) to the 2-ethyl crotonaldehyde concentration $C_{ECR}$ (ppm by mass) in the second acetic acid stream is, for example, not more than 35, preferably not more than 25, more preferably not more than 20, further preferably not more than 15. Since crotonaldehyde has a greater negative influence on a potassium permanganate test value than that of 2-ethyl crotonaldehyde, the potassium permanganate test value of product acetic acid is increased as the ratio ($C_{CR}/C_{ECR}$) is smaller.

The butyl acetate concentration in the second acetic acid stream is, for example, not more than 15 ppm by mass, preferably not more than 12 ppm by mass, more preferably not more than 10 ppm by mass, further preferably not more than 8 ppm by mass. The lower limit of the butyl acetate concentration in the second acetic acid stream is, for example, 0 ppm by mass (or 0.1 ppm by mass). A ratio ($C_{CR}/C_{BA}$) of the crotonaldehyde concentration $C_{CR}$ (ppm by mass) to the butyl acetate concentration $C_{BA}$ (ppm by mass) in the second acetic acid stream is, for example, not more than 2.0, preferably not more than 1.5, more preferably not more than 1.0, further preferably not more than 0.6. Since butyl acetate is harmless to the potassium permanganate test, the potassium permanganate test value of product acetic acid is increased as the ratio ($C_{CR}/C_{BA}$) is smaller.

To the second acetic acid stream flowing through the line 34, potassium hydroxide can be fed or added through the line 56 (potassium hydroxide introduction line). The potassium hydroxide can be fed or added, for example, as a solution such as an aqueous solution. Hydrogen iodide in the second acetic acid stream can be decreased by the feed or addition of potassium hydroxide to the second acetic acid stream. Specifically, the hydrogen iodide reacts with the potassium hydroxide to form potassium iodide and water. This can reduce the corrosion of an apparatus such as a distillation column ascribable to hydrogen iodide.

The distillation column 6 is a unit for performing the third distillation step and serves as the so-called higher boiling point component removal column in the present embodiment. The third distillation step is a step for further purifying acetic acid by the purification treatment of the second acetic acid stream continuously introduced to the distillation column 6. In the present embodiment, the step is not necessarily required. The distillation column 6 consists of, for example, a distillation column such as a plate column or a packed column. In the case of adopting a plate column as the distillation column 6, the theoretical number of plates thereof is, for example, 5 to 50, and the reflux ratio is, for example, 0.2 to 3000 according to the theoretical number of plates. In the inside of the distillation column 6 in the third distillation step, the column top pressure is set to, for example, −100 to 150 kPa (gauge pressure), and the column bottom pressure is higher than the column top pressure and is set to, for example, −90 to 180 kPa (gauge pressure). In the inside of the distillation column 6 in the third distillation step, the column top temperature is, for example, a temperature of higher than the boiling point of water and lower than the boiling point of acetic acid at the set column top pressure and is set to 50 to 150° C., and the column bottom temperature is, for example, a temperature of higher than the boiling point of acetic acid at the set column bottom pressure and is set to 70 to 160° C.

A vapor as an overhead stream is continuously withdrawn to the line 38 from the column top of the distillation column 6. A bottom fraction is continuously withdrawn to the line 39 from the column bottom of the distillation column 6. 6b denotes a reboiler. A side stream (liquid or gas) is continuously withdrawn to the line 46 from the height position between the column top and the column bottom of the distillation column 6. The connection position of the line 46 to the distillation column 6 may be, as shown in the drawing, higher than the connection position of the line 34 to the distillation column 6 in the height direction of the distillation column 6, but may be lower than the connection position of the line 34 to the distillation column 6 or may be the same as the connection position of the line 34 to the distillation column 6.

The vapor withdrawn from the column top of the distillation column 6 contains a larger amount of components having a lower boiling point (lower boiling point components) than that of acetic acid as compared with the bottom fraction from the distillation column 6 and contains, in addition to acetic acid, for example, methyl iodide, hydrogen iodide, water, methyl acetate, dimethyl ether, methanol, and formic acid. Such a vapor is continuously introduced to the condenser 6a through the line 38.

The condenser 6a separates the vapor from the distillation column 6 into a condensate portion and a gaseous portion by cooling and partial condensation. The condensate portion contains, in addition to acetic acid, for example, methyl iodide, hydrogen iodide, water, methyl acetate, dimethyl ether, methanol, and formic acid. At least a portion of the condensate portion is continuously refluxed to the distillation column 6 from the condenser 6a through the line 40. A portion (distillate) of the condensate portion may be recycled to the first acetic acid stream in the line 27 before introduction to the distillation column 5 from the condenser 6a through the lines 40, 41, and 42. Together with this or instead of this, a portion (distillate) of the condensate portion may be recycled to the vapor stream in the line 21 before introduction to the distillation column 3 from the condenser 6a through the lines 40, 41, and 43. Also, a portion (distillate) of the condensate portion may be recycled to the reaction vessel 1 from the condenser 6a through the lines 40, 44, and 23. Furthermore, as mentioned above, a portion of the distillate from the condenser 6a may be fed to the scrubber system 8 and used as an absorbing liquid in this system. In the scrubber system 8, a gaseous portion after absorption of a useful portion is discharged to the outside of the apparatus. Then, a liquid portion containing the useful components is introduced or recycled to the reaction vessel 1 from the scrubber system 8 through the recycle lines 48 and 23 and reused. In addition, a portion of the distillate from the condenser 6a may be led to various pumps (not shown) operated in the apparatus, through lines (not shown) and used as sealing solutions in these pumps. In addition, a portion of the distillate from the condenser 6a may be steadily withdrawn to the outside of the apparatus through a withdrawal line attached to the line 40, or may be non-steadily withdrawn to the outside of the apparatus when needed. In the case where a portion (distillate) of the condensate portion is removed from the distillation treatment system in the distillation column 6, the amount of the distillate (ratio of the distillate) is, for example, 0.01 to 30% by mass, preferably 0.1 to 10% by mass, more preferably 0.3 to 5% by mass, more preferably 0.5 to 3% by mass, of the condensate generated in the condenser 6a. On the other hand, the gaseous portion generated in the condenser 6a contains, for example, carbon monoxide, hydrogen, methane, carbon dioxide, nitrogen, oxygen, methyl iodide, hydrogen iodide, water, methyl acetate, acetic acid, dimethyl ether, methanol, acetaldehyde, and formic acid and is fed to the scrubber system 8 from the condenser 6a through the lines 45 and 15.

The bottom fraction withdrawn from the column bottom of the distillation column 6 through the line 39 contains a larger amount of components having a higher boiling point (higher boiling point components) than that of acetic acid as compared with the overhead stream from the distillation column 6 and contains, for example, acetate such as propionic acid and potassium acetate (in the case of feeding alkali such as potassium hydroxide to the line 34 etc.). Also, the bottom fraction withdrawn from the column bottom of the distillation column 6 through the line 39 also contains, for example, a corroded metal such as a metal formed at and released from the inside wall of a member constituting this acetic acid production apparatus, and a compound of iodine derived from corrosive iodine and the corroded metal, etc. In the present embodiment, such a bottom fraction is discharged to the outside of the acetic acid production apparatus.

The side stream continuously withdrawn to the line 46 from the distillation column 6 is continuously introduced as a third acetic acid stream to the next ion exchange resin column 7. This third acetic acid stream is more enriched with acetic acid than the second acetic acid stream continuously introduced to the distillation column 6. Specifically, the acetic acid concentration of the third acetic acid stream is higher than the acetic acid concentration of the second acetic acid stream. The acetic acid concentration of the third acetic acid stream is, for example, 99.8 to 99.999% by mass as long as being higher than the acetic acid concentration of the second acetic acid stream. In the present embodiment, the withdrawal position of the side stream from the distillation column 6 is higher than the introduction position of the second acetic acid stream to the distillation column 6 in the height direction of the distillation column 6. In another embodiment, the withdrawal position of the side stream from the distillation column 6 is the same as or lower than the introduction position of the second acetic acid stream to the distillation column 6 in the height direction of the distillation column 6. A simple distillator (evaporator) may be used in place of the distillation column 6. In particular, in the present invention, acetic acid having a very high potassium permanganate test value is obtained by a distillation treatment in the distillation column 5, therefore, the distillation column 6 can be omitted.

The ion exchange resin column 7 is a purification unit for performing the adsorptive removal step. This adsorptive removal step is a step for further purifying acetic acid by the adsorptive removal of, mainly, alkyl iodides (for example, ethyl iodide, propyl iodide, butyl iodide, hexyl iodide, decyl iodide, etc.) contained in a very small amount in the third acetic acid stream continuously introduced to the ion exchange resin column 7. The distillation column 6 may be omitted, and the second acetic acid stream from the distillation column 5 may be fed to the ion exchange resin column 7. The adsorptive removal step using the ion exchange resin column 7 may not be necessarily provided.

In the ion exchange resin column 7, an ion exchange resin having the ability to adsorb alkyl iodides is packed in the column to establish an ion exchange resin bed. Examples of such an ion exchange resin can include cation exchange resins in which a portion of leaving protons in an exchange group such as a sulfonic acid group, a carboxyl group, or a phosphonic acid group is substituted by a metal such as silver or copper. In the adsorptive removal step, for example, the third acetic acid stream (liquid) flows through the inside of the ion exchange resin column 7 packed with such an ion exchange resin, and in the course of this flow, impurities such as the alkyl iodides in the third acetic acid stream are adsorbed to the ion exchange resin and removed from the third acetic acid stream. In the ion exchange resin column 7 in the adsorptive removal step, the internal temperature is, for example, 18 to 100° C., and the rate of the acetic acid stream [the throughput of acetic acid per m$^3$ resin volume (m$^3$/h)] is, for example, 3 to 15 m$^3$/h·m$^3$ (resin volume).

A fourth acetic acid stream is continuously led to the line 47 from the lower end of the ion exchange resin column 7. The acetic acid concentration of the fourth acetic acid stream is higher than the acetic acid concentration of the third acetic acid stream. Specifically, the fourth acetic acid stream is more enriched with acetic acid than the third acetic acid stream continuously introduced to the ion exchange resin column 7. The acetic acid concentration of the fourth acetic acid stream is, for example, 99.9 to 99.999% by mass or not less than this range as long as being higher than the acetic acid concentration of the third acetic acid stream. In this production method, this fourth acetic acid stream can be retained in a product tank (not shown).

In this acetic acid production apparatus, a so-called product column or finishing column which is a distillation column may be disposed as a purification unit for further purifying the fourth acetic acid stream from the ion exchange resin column 7. In the case where such a product column is disposed, the product column consists of, for example, a distillation column such as a plate column or a packed column. In the case of adopting a plate column as the product column, the theoretical number of plates thereof is, for example, 5 to 50, and the reflux ratio is, for example, 0.5 to 3000 according to the theoretical number of plates. In the inside of the product column in the purification step, the column top pressure is set to, for example, −195 to 150 kPa (gauge pressure), and the column bottom pressure is higher than the column top pressure and is set to, for example, −190 to 180 kPa (gauge pressure). In the inside of the product column, the column top temperature is, for example, a temperature of higher than the boiling point of water and lower than the boiling point of acetic acid at the set column top pressure and is set to 50 to 150° C., and the column bottom temperature is, for example, a temperature of higher than the boiling point of acetic acid at the set column bottom pressure and is set to 70 to 160° C. A simple distillator (evaporator) may be used in place of the product column or the finishing column.

In the case of disposing the product column, the whole or a portion of the fourth acetic acid stream (liquid) from the ion exchange resin column 7 is continuously introduced to the product column. A vapor as an overhead stream containing a very small amount of lower boiling point components (e.g., methyl iodide, water, methyl acetate, dimethyl ether, crotonaldehyde, acetaldehyde, and formic acid) is continuously withdrawn from the column top of such a product column. This vapor is separated into a condensate portion and a gaseous portion in a predetermined condenser. A portion of the condensate portion is continuously refluxed to the product column, and another portion of the condensate portion may be recycled to the reaction vessel 1 or discarded to the outside of the system, or both. The gaseous portion is fed to the scrubber system 8. A bottom fraction containing a very small amount of higher boiling point components is continuously withdrawn from the column bottom of the product column. This bottom fraction is recycled to, for example, the second acetic acid stream in the line 34 before introduction to the distillation column 6. A side stream (liquid) is continuously withdrawn as a fifth acetic acid stream from the height position between the column top and the column bottom of the product column. The withdrawal position of the side stream from the product column is lower than, for example, the introduction position of the fourth acetic acid stream to the product column in the height direction of the product column. The fifth acetic acid stream is more enriched with acetic acid than the fourth acetic acid stream continuously introduced to the product column. Specifically, the acetic acid concentration of the fifth acetic acid stream is higher than the acetic acid concentration of the fourth acetic acid stream. The acetic acid concentration of the fifth acetic acid stream is, for example, 99.9 to 99.999% by mass or not less than this range as long as being higher than the acetic acid concentration of the fourth acetic acid stream. This fifth acetic acid stream is retained in, for example, a product tank (not shown). The ion exchange resin column 7 may be placed downstream of the product column instead of (or in addition to) its placement downstream of the distillation column 6 to treat the acetic acid stream from the product column.

EXAMPLES

Hereinafter, the present invention will be described in more detail with reference to Examples. However, the present invention is not intended to be limited by these Examples. All of parts, %, ppm, and ppb are based on mass. A water concentration was measured by the Karl Fischer water determination method; a metal ion concentration was measured by ICP analysis (or atomic adsorption analysis); and concentrations of other components were measured by gas chromatography.

Comparative Example 1

The following experiment was carried out in a methanol method acetic acid pilot plant (see FIG. 1).

Four hundred parts of a reaction mixture liquid [composition: 7.9% of methyl iodide (MeI), 2.1% of methyl acetate (MA), 2.5% of water ($H_2O$), 910 ppm of rhodium complex (in terms of Rh), 14.1% of lithium iodide (LiI), 110 ppm of propionic acid, 30 ppm of formic acid, 410 ppm of acetaldehyde (AD), 1.2 ppm of crotonaldehyde (CR), 1.2 ppm of 2-ethyl crotonaldehyde (2ECR), 9.9 ppm of butyl acetate (BA), acetic acid as a balance (however, containing a small amount of impurities)] obtained in a reaction vessel [total pressure of 2.8 MPa (absolute pressure), carbon monoxide partial pressure: 1.4 MPa (absolute pressure), hydrogen partial pressure: 0.02 MPa (absolute pressure), reaction temperature: 187° C.] were fed into an evaporator, and evaporated by 25%. One hundred parts of a stream [composition: 28.1% of methyl iodide, 4.9% of methyl acetate, 1.9% of water, 73 ppm of propionic acid, 85 ppm of formic acid, 1500 ppm of acetaldehyde, 2.5 ppm of crotonaldehyde, 0.09 ppm of 2-ethyl crotonaldehyde, 6.5 ppm of butyl acetate, acetic acid as the balance (however, containing a small amount of impurities)] in the evaporator were fed into a lower boiling point component removal column [20 actual plates, feed position: the second plate from the bottom, column top pressure of 250 kPa (absolute pressure), column top temperature of 140° C.] where a column top vapor was condensed to separate the column top vapor into an aqueous phase and an organic phase. Then, a portion (11 parts) of the organic phase was sent to an acetaldehyde removal column [80 actual plates, feed position: the eleventh plate from the bottom, column top pressure of 280 kPa (absolute pressure), column top temperature of 52° C.] where acetaldehyde was separated and removed out of a system, and the organic phase after removal of acetaldehyde was recycled to a reaction system. The remaining portion (41 parts) of the organic phase was directly recycled to the reaction system. A portion of the aqueous phase was refluxed (recycled) to the lower boiling point component removal column, and 1.5 parts of the remaining portion as a distillate liquid were recycled to the reaction system. Amount of the aqueous phase refluxed/amount of the distillate of the aqueous phase was defined as a reflux ratio, and the reflux ratio was set to 2. Three parts of the bottom fraction of the lower boiling point component removal column were withdrawn and recycled to the reaction system. Sixty-five parts of a side cut (SC) stream was withdrawn from the middle part (the fourth plate from the bottom) of the lower boiling point component removal column, and fed into a dehydration column [50 actual plates, feeding position: the thirty-fourth plate from the bottom, column top pressure of 295 kPa (absolute pressure), column top temperature of 150° C.]. A portion of a column top condensate of the dehydration column was refluxed (recycled) to the dehydration column, and 19 parts of the remaining portion as a distillate liquid was recycled to the reaction system. The reflux ratio of the dehydration column (amount refluxed/amount of the distillate) was set to 0.3. As a result, 46 parts of product acetic acid were obtained from the bottom fraction of the dehydration column. A crotonaldehyde content in product acetic acid was 2.2 ppm; a 2-ethyl crotonaldehyde content was 0.08 ppm; and a butyl acetate content was 13 ppm. The measured permanganate time (chameleon time) of product acetic acid was 5 minutes. The results are shown in Table 1.

Example 1

The same experiment as in Comparative Example 1 was conducted except that the hydrogen partial pressure of a reaction vessel was set to 0.07 MPa. The results are shown in Table 1.

Example 2

The same experiment as in Comparative Example 1 was conducted except that the amount of an organic phase of a column top condensate in a lower boiling point component removal column fed to an acetaldehyde removal column was set to 21 parts. With this change, a reaction mixture liquid composition and a vapor composition in an evaporator were changed. The results are shown in Table 1.

Example 3

The same experiment as in Comparative Example 1 was conducted except that the reflux ratio of a lower boiling point component removal column was set to 5, and the reflux ratio of a dehydration column was set to 0.5. With this change, a reaction mixture liquid composition and a vapor composition in an evaporator were changed. The results are shown in Table 1.

Example 4

The same experiment as in Comparative Example 1 was conducted except that the reflux ratio of a lower boiling point component removal column was set to 5; the reflux ratio of a dehydration column was set to 0.5; and the amount of an organic phase of a column top condensate in the lower boiling point component removal column fed to an acetaldehyde removal column was set to 21 parts. With this change, a reaction mixture liquid composition and a vapor composition in an evaporator were changed. The results are shown in Table 1.

Example 5

The same experiment as in Comparative Example 1 was conducted except that the reflux ratio of a lower boiling point component removal column was set to 10; the reflux ratio of a dehydration column was set to 5; and the amount of an organic phase of a column top condensate in the lower boiling point component removal column fed to an acetaldehyde removal column was set to 21 parts. With this change, a reaction mixture liquid composition and a vapor composition in an evaporator were changed. The results are shown in Table 1.

Example 6

The same experiment as in Comparative Example 1 was conducted except that the reflux ratio of a lower boiling point component removal column was set to 15; the reflux ratio of a dehydration column was set to 10; and the amount of an organic phase of a column top condensate in the lower boiling point component removal column fed to an acetaldehyde removal column was set to 21 parts. With this change, a reaction mixture liquid composition and a vapor composition in an evaporator were changed. The results are shown in Table 1.

Example 7

The same experiment as in Comparative Example 1 was conducted except that the reflux ratio of a lower boiling point component removal column was set to 20; the reflux ratio of a dehydration column was set to 20; and the amount of an organic phase of a column top condensate in the lower boiling point component removal column fed to an acetaldehyde removal column was set to 21 parts. With this change, a reaction mixture liquid composition and a vapor composition in an evaporator were changed. The results are shown in Table 1.

In Table 1, $C_{AD}$ represents an acetaldehyde concentration; $C_{CR}$ represents a crotonaldehyde concentration; $C_{EDR}$ represents a 2-ethyl crotonaldehyde concentration; and $C_{BA}$ represents a butyl acetate concentration.

TABLE 1

|  |  | Comparative Example | Examples | | | | | | |
|---|---|---|---|---|---|---|---|---|---|
|  |  | 1 | 1 | 2 | 3 | 4 | 5 | 6 | 7 |
| Hydrogen partial pressure of reaction vessel (MPa) |  | 0.02 | 0.07 | 0.02 | 0.02 | 0.02 | 0.02 | 0.02 | 0.02 |
| Reflux ratio of lower boiling point component removal column |  | 2 | 2 | 2 | 5 | 5 | 10 | 15 | 20 |
| Reflux ratio of dehydration column |  | 0.3 | 0.3 | 0.3 | 0.5 | 0.5 | 5 | 10 | 20 |
| Reaction mixture liquid | $C_{AD}$ (ppm) | 410 | 410 | 220 | 400 | 210 | 210 | 210 | 220 |
|  | $C_{CR}$ (ppm) | 1.2 | 0.9 | 0.9 | 1.2 | 0.9 | 0.9 | 0.9 | 0.9 |
|  | $C_{ECR}$ (ppm) | 1.2 | 1.2 | 1.3 | 1.2 | 1.4 | 1.5 | 1.7 | 1.8 |
|  | $C_{BA}$ (ppm) | 9.9 | 10 | 8.4 | 10 | 8.5 | 8.5 | 8.6 | 8.6 |
| Feeding to lower boiling point component removal column | $C_{CR}$ (ppm) | 2.5 | 1.1 | 1.2 | 2.6 | 1.2 | 1.3 | 1.1 | 1.1 |
|  | $C_{ECR}$ (ppm) | 0.09 | 0.06 | 0.20 | 0.09 | 0.21 | 0.28 | 0.35 | 0.39 |
|  | $C_{BA}$ (ppm) | 6.5 | 6.7 | 0.57 | 7.1 | 0.9 | 1.1 | 1.3 | 1.5 |
| Side cut liquid of lower boiling point component removal column | $C_{CR}$ (ppm) | 2.4 | 1.0 | 1.1 | 1.9 | 0.9 | 0.7 | 0.4 | 0.3 |
|  | $C_{ECR}$ (ppm) | 0.06 | 0.03 | 0.22 | 0.06 | 0.24 | 0.35 | 0.46 | 0.52 |
|  | $C_{BA}$ (ppm) | 9.3 | 9.6 | 0.6 | 10 | 1.1 | 1.4 | 1.7 | 2.0 |
|  | $C_{CR}/C_{ECR}$ | 40 | 33 | 5.0 | 32 | 3.8 | 2.0 | 0.87 | 0.58 |
|  | $C_{CR}/C_{BA}$ | 0.26 | 0.10 | 1.8 | 0.19 | 0.82 | 0.50 | 0.24 | 0.15 |
| Bottom fraction of dehydration column (product) | $C_{CR}$ (ppm) | 2.2 | 0.94 | 0.99 | 1.8 | 0.83 | 0.56 | 0.26 | 0.17 |
|  | $C_{ECR}$ (ppm) | 0.08 | 0.04 | 0.03 | 0.08 | 0.05 | 0.13 | 0.18 | 0.25 |
|  | $C_{BA}$ (ppm) | 13 | 13 | 0.76 | 14 | 1.5 | 1.8 | 2.3 | 2.7 |
|  | $C_{CR}/C_{ECR}$ | 28 | 24 | 33 | 23 | 17 | 4.3 | 1.4 | 0.68 |
|  | $C_{CR}/C_{BA}$ | 0.17 | 0.07 | 1.3 | 0.13 | 0.55 | 0.31 | 0.11 | 0.06 |
| Product chameleon time (minutes) |  | 5 | 60 | 50 | 10 | 90 | 150 | 180 | 240 |

[Discussion on Results]

From the comparison of Comparative Example 1 and Example 1, it is evident that a product chameleon time is increased when the hydrogen partial pressure of the reaction vessel is increased. This is considered as follows. Since the high hydrogen partial pressure of the reaction vessel increases the amount of crotonaldehyde (CR) hydrogenated, a CR concentration in a charging mixture of the lower boiling point component removal column and a CR concentration in a side cut liquid (first acetic acid stream) of the lower boiling point component removal column are decreased. As a result, a CR concentration in a second acetic acid stream obtained in the dehydration column is decreased to increase the product chameleon time.

From the comparison of Comparative Example 1 and Example 2 and the comparison of Example 3 and Example 4, it is evident that an increase in the amount (amount of AD removed) of the organic phase of the column top condensate of the lower boiling point component removal column fed to the acetaldehyde removal column increases a product chameleon time. This is considered as follows. Since an increase in the amount of AD removed decreases an AD concentration in a recycle liquid to the reaction vessel to decrease an amount of CR produced in the reaction vessel, a CR concentration in the charging mixture of the lower boiling point component removal column and a CR concentration in a side cut liquid (first acetic acid stream) of the lower boiling point component removal column are decreased. As a result, a CR concentration in a second acetic acid stream obtained in the dehydration column is decreased to increase the product chameleon time. When the amount of the lower boiling point component removal column and/or the dehydration column refluxed is increased, CR is concentrated to the column top, which increases a CR concentration of the recycle liquid of the reaction vessel to increase 2-ethyl crotonaldehyde (2ECR) in the reaction of CR+AD→2-ethyl crotonaldehyde. This increases 2ECR concentrations in the charging mixture of the lower boiling point component removal column, the first acetic acid stream, and the second acetic acid stream to some extent, but 2ECR has lower sensitivity to a chameleon time than that of CR, which increases the product chameleon time as a whole.

From the comparison of Comparative Example 1 and Example 3 and the comparison of Comparative Example 1 and Examples 2 and 4 to 7, the following are evident. An amount of AD removed is small, and an amount of AD recycled to the reaction vessel is relatively large. Therefore, when the reflux ratio of the lower boiling point component removal column or the dehydration column is increased to concentrate CR to the column top even if the AD concentration in the reaction mixture liquid is high, and the column top condense in which CR is concentrated is recycled to the reaction vessel, CR concentrations in a side cut liquid of the lower boiling point component removal column (first acetic acid stream) and a second acetic acid stream obtained in the dehydration column are decreased, which increase a product chameleon time. CR is hydrogenated in the reaction vessel, followed by esterifying, to be converted into butyl acetate (BA). BA concentrations in the charging mixture of the lower boiling point component removal column, the side cut liquid (first acetic acid stream) of the lower boiling point component removal column, and the second acetic acid stream obtained in the dehydration column are increased, but BA has no effect on a chameleon time.

The reflux ratios of the lower boiling point component removal column and the dehydration column are simultaneously changed in Examples 3 to 7. However, even if only one of the reflux ratios is increased, CR is concentrated to the column top, and a harmless mechanism in the reaction vessel provided by recycling the column top condensate in which CR is concentrated to the reaction vessel is the same.

The above results provided the following findings. The hydrogen partial pressure of the reaction vessel is increased, or the reflux ratio of the lower boiling point component removal column is increased, to control the CR concentration in the first acetic acid stream to not more than a specific value, or to control the reflux ratio of the dehydration column to not less than a constant value, which can increase the chameleon time of product acetic acid. When the hydrogen partial pressure of the reaction vessel is increased, or the reflux ratio of the lower boiling point component removal column and/or the dehydration column is increased to concentrate CR to the column top for recycling CR to the reaction vessel, the reactions of CR+AD→2ECR, CR+$H_2$→butyl alcohol, and butyl alcohol+acetic acid→BA progress in the reaction vessel, as described above, which provides harmless crotonaldehyde or a decrease in harmful crotonaldehyde. As a result, it is considered that the chameleon time of product acetic acid is increased. The AD removal treatment may not be necessarily carried out. It was confirmed that the AD removal treatment more improves the quality of product acetic acid.

In conclusion, the composition of the present invention and its variations are appended below.

[1] A method for producing acetic acid, comprises:

a carbonylation reaction step of reacting methanol with carbon monoxide in the presence of a catalyst system containing a metal catalyst and methyl iodide, as well as acetic acid, methyl acetate, and water in a reaction vessel to produce acetic acid;

an evaporation step of separating a reaction mixture obtained in the carbonylation reaction step into a vapor stream and a residual liquid stream in an evaporator;

a lower boiling point component removal step of separating the vapor stream by a first distillation column into a first overhead stream rich in at least one lower boiling point component selected from methyl iodide and acetaldehyde, and a first acetic acid stream rich in acetic acid, and condensing and separating the first overhead stream to obtain an aqueous phase and an organic phase; and a first overhead stream recycle step of recycling at least a portion of the aqueous phase and/or the organic phase obtained by condensing the first overhead stream to the reaction vessel, wherein a crotonaldehyde concentration in the first acetic acid stream is controlled to not more than 2.2 ppm by mass.

[2] A method for producing acetic acid, comprises:

a carbonylation reaction step of reacting methanol with carbon monoxide in the presence of a catalyst system containing a metal catalyst and methyl iodide, as well as acetic acid, methyl acetate, and water in a reaction vessel to produce acetic acid;

an evaporation step of separating a reaction mixture obtained in the carbonylation reaction step into a vapor stream and a residual liquid stream in an evaporator;

a lower boiling point component removal step of separating the vapor stream by a first distillation column into a first overhead stream rich in at least one lower boiling point component selected from methyl iodide and acetaldehyde, and a first acetic acid stream rich in acetic acid, and condensing and separating the first overhead stream to obtain an aqueous phase and an organic phase;

a dehydration step of separating the first acetic acid stream by a second distillation column into a second overhead stream rich in water and a second acetic acid stream more enriched with acetic acid than the first acetic acid stream; and an overhead stream recycle step of recycling at least a portion of the aqueous phase and/or the organic phase obtained by condensing the first overhead stream, and/or a portion of the second overhead stream to the reaction vessel, wherein a crotonaldehyde concentration in the first acetic acid stream is controlled to not more than 2.2 ppm by mass, and/or a reflux ratio of the second distillation column is controlled to not less than 0.32.

[3] The method for producing acetic acid according to [2], wherein a crotonaldehyde concentration in the second acetic acid stream is not more than 2.0 ppm by mass (preferably not more than 1.8 ppm by mass, more preferably not more than 1.5 ppm by mass, further preferably not more than 1.2 ppm by mass, particularly preferably not more than 0.7 ppm by mass, especially, not more than 0.5 ppm by mass).

[4] The method for producing acetic acid according to [2] or [3], wherein a 2-ethyl crotonaldehyde concentration in the second acetic acid stream is not more than 3.0 ppm by mass (preferably not more than 1.8 ppm by mass, more preferably not more than 1.5 ppm by mass, further preferably not more than 1.2 ppm by mass, particularly preferably not more than 0.7 ppm by mass, especially, not more than 0.5 ppm by mass).

[5] The method for producing acetic acid according to any one of [2] to [4], wherein a ratio ($C_{CR}/C_{ECR}$) of the crotonaldehyde concentration $C_{CR}$ (ppm by mass) to the 2-ethyl crotonaldehyde concentration $C_{ECR}$ (ppm by mass) in the second acetic acid stream is not more than 35 (preferably not more than 25, more preferably not more than 20, further preferably not more than 15).

[6] The method for producing acetic acid according to any one of [2] to [5], wherein a butyl acetate concentration in the second acetic acid stream is not more than 15 ppm by mass (preferably not more than 12 ppm by mass, more preferably not more than 10 ppm by mass, further preferably not more than 8 ppm by mass).

[7] The method for producing acetic acid according to any one of [2] to [6], wherein a ratio ($C_{CR}/C_{BA}$) of the crotonaldehyde concentration $C_{CR}$ (ppm by mass) to the butyl acetate concentration $C_{BA}$ (ppm by mass) in the second acetic acid stream is not more than 2.0 (preferably not more than 1.5, more preferably not more than 1.0, further preferably not more than 0.6).

[8] The method for producing acetic acid according to any one of [2] to [7], wherein a reflux ratio of the second distillation column is controlled to not less than 0.35 (preferably not less than 0.4, more preferably not less than 1, further preferably not less than 2).

[9] The method for producing acetic acid according to any one of [2] to [8], wherein the upper limit of the reflux ratio of the second distillation column is 3000 (preferably 1000, more preferably 100, further preferably on the order of 10).

[10] The method for producing acetic acid according to any one of [1] to [9], wherein the catalyst system further contains an ionic iodide.

[11] The method for producing acetic acid according to any one of [1] to [10], further comprising an acetaldehyde separation and removal step of distilling at least a portion of the aqueous phase and/or the organic phase obtained by condensing the first overhead stream, to separate and remove acetaldehyde.

[12] The method for producing acetic acid according to [11], wherein at least a portion of a residual liquid after separating and removing the acetaldehyde from at least a portion of the aqueous phase and/or the organic phase is recycled to the reaction vessel.

[13] The method for producing acetic acid according to any one of [1] to [12], wherein, for an operating condition of the first distillation column, when only the aqueous phase is refluxed to the first distillation column, a reflux ratio of the aqueous phase is not less than 2 (preferably not less than 3, more preferably not less than 4, further preferably not less than 8, particularly preferably not less than 10); when only the organic phase is refluxed, a reflux ratio of the organic phase is not less than 1 (preferably not less than 1.5, more preferably not less than 2, further preferably not less than 4, particularly preferably not less than 5); and when both the aqueous phase and the organic phase are refluxed, a total reflux ratio of the aqueous phase and the organic phase is not less than 1.5 (preferably not less than 2.3, more preferably not less than 3, further preferably not less than 6, particularly preferably not less than 7.5).

[14] The method for producing acetic acid according to any one of [1] to [13], wherein a hydrogen partial pressure of the reaction vessel is not less than 0.01 MPa (absolute pressure), preferably not less than 0.015 MPa (absolute pressure), more preferably not less than 0.02 MPa (absolute pressure), further preferably not less than 0.04 MPa (absolute pressure), particularly preferably not less than 0.06 MPa (absolute pressure), especially, not less than 0.07 MPa (absolute pressure)).

[15] The method for producing acetic acid according to any one of [1] to [14], wherein an acetaldehyde concentration in a reaction mixture liquid of the reaction vessel is not more than 500 ppm by mass (preferably not more than 450 ppm by mass, more preferably not more than 400 ppm by mass, further preferably not more than 350 ppm by mass, particularly preferably not more than 300 ppm by mass, especially, not more than 250 ppm by mass).

[16] The method for producing acetic acid according to any one of [1] to [15], wherein a 2-ethyl crotonaldehyde concentration in the first acetic acid stream is not more than 3.0 ppm by mass (preferably not more than 2.0 ppm by mass, more preferably not more than 1.0 ppm by mass, further preferably not more than 0.8 ppm by mass, particularly preferably not more than 0.5 ppm by mass).

[17] The method for producing acetic acid according to any one of [1] to [16], wherein a ratio ($C_{CR}/C_{ECR}$) of the crotonaldehyde concentration $C_{CR}$ (ppm by mass) to the 2-ethyl crotonaldehyde concentration $C_{ECR}$ (ppm by mass) in the first acetic acid stream is not more than 35 (preferably not more than 25, more preferably not more than 20, further preferably not more than 15).

[18] The method for producing acetic acid according to any one of [1] to [17], wherein a butyl acetate concentration in the first acetic acid stream is not more than 15 ppm by mass (preferably not more than 12 ppm by mass, more preferably not more than 10 ppm by mass, further preferably not more than 8 ppm by mass).

[19] The method for producing acetic acid according to any one of [1] to [18], wherein a ratio ($C_{CR}/C_{BA}$) of the crotonaldehyde concentration $C_{CR}$ (ppm by mass) to the butyl acetate concentration $C_{BA}$ (ppm by mass) in the first acetic acid stream is not more than 2.0 (preferably not more than 1.5, more preferably not more than 1.0, further preferably not more than 0.6).

[20] The method for producing acetic acid according to any one of [1] to [19], wherein the crotonaldehyde concentration in the first acetic acid stream is controlled to not more than 2.0 ppm by mass (preferably not more than 1.8 ppm by mass, more preferably not more than 1.5 ppm by mass, further preferably not more than 1.2 ppm by mass, particularly preferably not more than 1.0 ppm by mass, especially, not more than 0.8 ppm by mass, among others, not more than 0.5 ppm by mass).

[21] The method for producing acetic acid according to any one of [1] to [20], wherein a hydrogen partial pressure of the reaction vessel is not more than 0.5 MPa (absolute pressure) (preferably not more than 0.2 MPa (absolute pressure)).

[22] The method for producing acetic acid according to any one of [1] to [21], wherein a reflux ratio of the first distillation column is not less than 0.5.

[23] The method for producing acetic acid according to any one of [1] to [22], wherein the upper limit of the reflux ratio of the first distillation column is 3000 (preferably 1000, more preferably 100, further preferably 30).

[24] The method for producing acetic acid according to any one of [1] to [23], wherein a crotonaldehyde concentration in a reaction mixture liquid of the reaction vessel is not more than 5 ppm by mass (preferably not more than 3 ppm by mass, more preferably not more than 2 ppm by mass).

[25] The method for producing acetic acid according to any one of [1] to [24], wherein a 2-ethyl crotonaldehyde concentration in the reaction mixture liquid of the reaction vessel is not more than 5 ppm by mass (preferably not more than 3 ppm by mass, more preferably not more than 2 ppm by mass).

[26] The method for producing acetic acid according to any one of [1] to [25], wherein a butyl acetate concentration in the reaction mixture liquid of the reaction vessel is 0.1 to 15 ppm by mass (preferably 1 to 12 ppm by mass, more preferably 2 to 9 ppm by mass).

[27] The method for producing acetic acid according to any one of [1] to [26], wherein a crotonaldehyde concentration in the vapor stream is 0 to 5 ppm by mass (preferably 0.1 to 3 ppm by mass, more preferably 0.2 to 2 ppm by mass).

[28] The method for producing acetic acid according to any one of [1] to [27], wherein a 2-ethyl crotonaldehyde concentration in the vapor stream is 0 to 3 ppm by mass (preferably 0.02 to 2 ppm by mass, more preferably 0.03 to 0.8 ppm by mass).

[29] The method for producing acetic acid according to any one of [1] to [28], wherein a butyl acetate concentration in the vapor stream is 0.1 to 13 ppm by mass (preferably 0.2 to 12 ppm by mass, more preferably 0.3 to 9 ppm by mass).

INDUSTRIAL APPLICABILITY

A method for producing acetic acid according to the present invention can be used as a method industrial for producing acetic acid by a carbonylation process of a methanol method (an acetic acid process of a methanol method).

REFERENCE SIGNS LIST

1: reaction vessel
2: evaporator
3, 5, and 6: distillation column
4: decanter
7: ion exchange resin column
8: scrubber system
9: acetaldehyde separation and removal system
16: reaction mixture feed line
17: vapor stream discharge line
18 and 19: residual liquid stream recycle line
54: carbon monoxide-containing gas introduction line
55 and 56: potassium hydroxide introduction line
57: catalyst circulating pump
91: distillation column (first acetaldehyde removal column)
92: extraction column
93: distillation column (second acetaldehyde removal column)
94: distillation column (extractive distillation column)
95: decanter
96: decanter
97: distillation column (acetaldehyde removal column)
98: distillation column (extractive distillation column)
99: decanter
200: chimney tray

The invention claimed is:

1. A method for producing acetic acid, comprising:
a carbonylation reaction step of reacting methanol with carbon monoxide in the presence of a catalyst system containing a metal catalyst and methyl iodide, as well as acetic acid, methyl acetate, and water in a reaction vessel to produce acetic acid;
an evaporation step of separating a reaction mixture obtained in the carbonylation reaction step into a vapor stream and a residual liquid stream in an evaporator;
a lower boiling point component removal step of separating the vapor stream by a first distillation column into a first overhead stream rich in at least one lower boiling point component selected from methyl iodide and acetaldehyde, and a first acetic acid stream rich in acetic acid, and condensing and separating the first overhead stream to obtain an aqueous phase and an organic phase; and
a first overhead stream recycle step of recycling at least a portion of the aqueous phase and/or the organic phase obtained by condensing the first overhead stream to the reaction vessel,
wherein a crotonaldehyde concentration in the first acetic acid stream is controlled to not more than 2.2 ppm by mass; and
a ratio of $C_{CR}/C_{ECR}$ of the crotonaldehyde concentration $C_{CR}$ in ppm by mass to the 2-ethyl crotonaldehyde concentration $C_{ECR}$ in ppm by mass in the first acetic acid stream is not more than 35;
further wherein the ratio of $C_{CR}/C_{ECR}$ of the crotonaldehyde concentration $C_{CR}$ in ppm by mass to the 2-ethyl crotonaldehyde concentration $C_{ECR}$ in ppm by mass in the first acetic acid stream is controlled to be not more than 35 by at least one of (a) controlling a hydrogen partial pressure in the reaction vessel to not less than 0.02 MPa and no more than 0.5 MPa or (b) controlling a reflux ratio during the lower boiling point component removal step to not less than 2 and no more than 100.

2. The method for producing acetic acid according to claim 1, further comprising:
a dehydration step of separating the first acetic acid stream by a second distillation column into a second overhead stream rich in water and a second acetic acid stream more enriched with acetic acid than the first acetic acid stream; and
an overhead stream recycle step of recycling at least a portion of the aqueous phase and/or the organic phase obtained by condensing the first overhead stream, and/or a portion of the second overhead stream to the reaction vessel,
wherein the crotonaldehyde concentration in the first acetic acid stream is controlled to not more than 2.2 ppm by mass, and a reflux ratio of the second distillation column is controlled to not less than 0.32 and no more than 100.

3. The method for producing acetic acid according to claim 2, wherein a crotonaldehyde concentration in the second acetic acid stream is not more than 2.0 ppm by mass.

4. The method for producing acetic acid according to claim 2, wherein a 2-ethyl crotonaldehyde concentration in the second acetic acid stream is not more than 3.0 ppm by mass.

5. The method for producing acetic acid according to claim 2, wherein a ratio of $C_{CR}/C_{ECR}$ of the crotonaldehyde concentration $C_{CR}$ in ppm by mass to the 2-ethyl crotonaldehyde concentration $C_{ECR}$ in ppm by mass in the second acetic acid stream is not more than 35.

6. The method for producing acetic acid according to claim 2, wherein a butyl acetate concentration in the second acetic acid stream is not more than 15 ppm by mass.

7. The method for producing acetic acid according to claim 2, wherein a ratio of $C_{CR}/C_{BA}$ of the crotonaldehyde concentration $C_{CR}$ in ppm by mass to the butyl acetate concentration $C_{BA}$ in ppm by mass in the second acetic acid stream is not more than 2.0.

8. The method for producing acetic acid according to claim 1, wherein the catalyst system further contains an ionic iodide.

9. The method for producing acetic acid according to claim 1, further comprising an acetaldehyde separation and removal step of distilling at least a portion of the aqueous phase and/or the organic phase obtained by condensing the first overhead stream, to separate and remove acetaldehyde.

10. The method for producing acetic acid according to claim 9, wherein at least a portion of a residual liquid after separating and removing the acetaldehyde from at least a portion of the aqueous phase and/or the organic phase is recycled to the reaction vessel.

11. The method for producing acetic acid according to claim 1, wherein, for an operating condition of the first distillation column, when only the aqueous phase is refluxed to the first distillation column, a reflux ratio of the aqueous phase is not less than 2 and no more than 100; when only the organic phase is refluxed, a reflux ratio of the organic phase is not less than 1 and no more than 100; and when both the aqueous phase and the organic phase are refluxed, a total reflux ratio of the aqueous phase and the organic phase is not less than 1.5 and no more than 100.

12. The method for producing acetic acid according to claim 1, wherein a hydrogen partial pressure of the reaction vessel is not less than 0.01 MPa.

13. The method for producing acetic acid according to claim 1, wherein an acetaldehyde concentration in a reaction mixture liquid of the reaction vessel is not more than 500 ppm by mass.

14. The method for producing acetic acid according to claim 1, wherein a 2-ethyl crotonaldehyde concentration in the first acetic acid stream is not more than 3.0 ppm by mass.

15. The method for producing acetic acid according to claim 1, wherein a butyl acetate concentration in the first acetic acid stream is not more than 15 ppm by mass.

16. The method for producing acetic acid according to claim 1, wherein a ratio of $C_{CR}/C_{BA}$ of the crotonaldehyde concentration $C_{CR}$ in ppm by mass to the butyl acetate concentration $C_{BA}$ in ppm by mass in the first acetic acid stream is not more than 2.0.

17. The method for producing acetic acid according to claim 1, wherein the ratio of $C_{CR}/C_{ECR}$ of the crotonaldehyde concentration $C_{CR}$ in ppm by mass to the 2-ethyl crotonaldehyde concentration $C_{ECR}$ in ppm by mass in the first acetic acid stream is controlled to be not more than 35 by (a) controlling a hydrogen partial pressure in the reaction vessel to not less than 0.01 MPa and no more than 0.5 MPa.

18. The method for producing acetic acid according to claim 1, wherein the ratio of $C_{CR}/C_{ECR}$ of the crotonaldehyde concentration $C_{CR}$ in ppm by mass to the 2-ethyl crotonaldehyde concentration $C_{ECR}$ in ppm by mass in the first acetic acid stream is controlled to be not more than 35 by (b) controlling a reflux ratio during the lower boiling point component removal step to not less than 2 and no more than 100.

19. The method for producing acetic acid according to claim 2, wherein the ratio of $C_{CR}/C_{ECR}$ of the crotonaldehyde concentration $C_{CR}$ in ppm by mass to the 2-ethyl crotonaldehyde concentration $C_{ECR}$ in ppm by mass in the first acetic acid stream is controlled to be not more than 35 by (a) controlling a hydrogen partial pressure in the reaction vessel to not less than 0.01 MPa and no more than 0.5 MPa.

20. The method for producing acetic acid according to claim 2, wherein the ratio of $C_{CR}/C_{ECR}$ of the crotonaldehyde concentration $C_{CR}$ in ppm by mass to the 2-ethyl crotonaldehyde concentration $C_{ECR}$ in ppm by mass in the first acetic acid stream is controlled to be not more than 35 by (b) controlling a reflux ratio during the lower boiling point component removal step to not less than 2 and no more than 100.

21. The method for producing acetic acid according to claim 2, wherein the ratio of $C_{CR}/C_{ECR}$ of the crotonaldehyde concentration $C_{CR}$ in ppm by mass to the 2-ethyl crotonaldehyde concentration $C_{ECR}$ in ppm by mass in the first acetic acid stream is controlled to be not more than 35 by (c) controlling a reflux ratio of the second distillation column to not less than 0.32 and no more than 100.

* * * * *